(12) United States Patent
Fisher et al.

(10) Patent No.: US 6,982,148 B2
(45) Date of Patent: Jan. 3, 2006

(54) PROGRESSIVE ELEVATED GENE-3 (PEG-3) INDUCES AGGRESSIVE CANCER PHENOTYPE AND REGULATES ANGIOGENESIS

(75) Inventors: Paul B. Fisher, Scarsdale, NY (US); Zao-Zhong Su, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 200 days.

(21) Appl. No.: 10/177,811

(22) Filed: Jun. 20, 2002

(65) Prior Publication Data

US 2003/0044828 A1    Mar. 6, 2003

Related U.S. Application Data

(63) Continuation of application No. PCT/US00/34564, filed on Dec. 20, 2000.

(60) Provisional application No. 60/173,114, filed on Dec. 27, 1999.

(51) Int. Cl.
*C12Q 1/68*    (2006.01)

(52) U.S. Cl. .............................. 435/6; 435/29; 435/32
(58) Field of Classification Search .................... 435/6, 435/29, 32
See application file for complete search history.

(56) References Cited

U.S. PATENT DOCUMENTS 6,146,877 A    11/2000    Fisher

FOREIGN PATENT DOCUMENTS

WO    WO 9937776    7/1999
WO    WO 9949898    10/1999

OTHER PUBLICATIONS

Su et al. PEG-3, a nontransforming cancer progression gene, is a positive regulator of cancer aggresiveness and angiogenesis PNAS vol. 96 No. 26 pp15115-15120 Dec. 21, 1999.*
Su et al., 1999, "PEG-3, a nontransforming cancer progression gene, is a positive regulator of cancer aggresiveness and angiogenesis", PNAS 96:15115-15120.

* cited by examiner

*Primary Examiner*—James Keitter
*Assistant Examiner*—Konstantina Katcheves
(74) *Attorney, Agent, or Firm*—Baker Botts LLP

(57) ABSTRACT

The present invention provides a method for identifying a gene which is expressed at a modulated level in an aggressive cancer by: (a) measuring baseline expression levels of genes in cancer cells; (b) introducing into the cancer cells an expression vector which directs expression of rat PEG-3; (c) measuring the expression levels of genes in the cells from step (b); and (d) identifying genes, the expression of which is modulated in an aggressive cancer. In another aspect of this invention, the measurement of expression levels of genes in step (a) and/or step (c) comprises measuring mRNA levels. In yet another aspect of the invention, the measurement of expression levels of genes in step (a) and/or step (c) comprises measuring RNA levels. In another aspect of the invention, the genes identified in step (d) are used for diagnosing whether a subject suffers from an aggressive form of cancer.

2 Claims, 10 Drawing Sheets

PEG-3

VEGF

Ad5 E1A

GAPDH

VEGF PROTEIN

PROGRESSIVE ELEVATED GENE-3 (PEG-3) INDUCES AGGRESSIVE CANCER PHENOTYPE AND REGULATES ANGIOGENESIS

This application is a continuation-in-part and claims priority of U.S. Provisional Application No. 60/173,114, filed Dec. 20, 1999, the contents of which are hereby incorporated by reference.

This invention was made in part with government funds under Grants CA35675, CA73264 and GM31452 from the National Science Foundation. Therefore, the U.S. Government has certain rights in the invention.

Throughout this application, various publications are referred to by Arabic numeral within parentheses. Full citations for these publications are presented immediately before the claims. Disclosures of these publications in their entireties are hereby incorporated by reference in order too more fully describe the state of the art as known to those skilled therein as of the date of the invention described and claimed herein.

BACKGROUND OF THE INVENTION

Cancer is a progressive disease culminating in acquisition of metastatic potential by a subset of evolving tumor cells. Generation of an adequate blood supply in tumors by production of new blood vessels, angiogenesis, is a defining element in this process. Although extensively investigated, the precise molecular events underlying tumor development, cancer progression and angiogenesis remain unclear. Subtraction hybridization identified a novel genetic element, progression elevated gene-3 (PEG-3), whose expression directly correlates with cancer progression and acquisition of oncogenic potential by transformed rodent cells. As demonstrated herein, forced expression of PEG-3 in tumorigenic rodent cells, and in human cancer cells, increases their oncogenic potential in nude mice as reflected by a shorter tumor latency time and the production of larger tumors with increased vascularization. Moreover, inhibiting endogenous PEG-3 expression in progressed rodent cancer cells by stable expression of an antisense expression vector extinguishes the progressed cancer phenotype. Cancer aggressiveness of PEG-3 expressing rodent cells correlates directly with increased RNA transcription, elevated mRNA levels and augmented secretion of vascular endothelial growth factor (VEGF). Furthermore, transient ectopic expression of PEG-3 transcriptionally activates PEG-3 in transformed rodent and human cancer cells. Taken together these data demonstrate that PEG-3 is a positive regulator of cancer aggressiveness, a process regulated by augmented VEGF production. These studies also support an association between expression of a single non-transforming cancer progression inducing gene, PEG-3, and the processes of cancer aggressiveness and angiogenesis.

Genetic changes implicated in cancer development and progression include oncogene activation and tumor suppressor gene inactivation (1–4). Recent studies suggest an additional component to this paradigm, involving genes that are associated with and may directly mediate (progression elevated genes, (PEGen)) or suppress (progression suppressed genes, (PSGen)) cancer aggressiveness and tumor progression (3,4). One PEGen, PEG-3, was identified as a gene displaying elevated expression as a consequence of cancer progression and DNA damage in rodent tumor cells (3). A fundamental question in cancer biology is the mechanism by which these diverse genetic elements interact in mediating tumor development and progression.

An important event in controlling the growth of both primary and metastatic tumors is angiogenesis (5–9). Without neovascularization (formation of new blood vessels), tumors usually do not grow beyond a few $mm^3$ in size (5–7). The formation of new tumor-associated neovascularization is responsible for the increased perfusion of nutrients and oxygen into the tumor mass and the removal of waste products. This process also facilitates entry of tumor cells into the circulatory system, a prerequisite for metastasis. Consistent with this finding, a high degree of tumor vascularization directly correlates with an increase in a tumor's malignant phenotype and inversely correlates with patient survival (10–12). Production of new blood vessels by the developing tumor and distant metastases results from the elaboration if large quantities of angiogenic molecules by both the tumor and host cells (5–9). The balance between positive and negative regulators of this process (8,9) controls the degree of angiogenesis. These observations emphasize that any genetic modification in a cancer cell that culminates in expansion of tumor growth and metastasis will be inexorably linked to angiogenesis.

Transformation of early passage rat embryo cells by adenovirus type 5 (Ad5) is a progressive process in which morphologically transformed cells temporally acquire new and exhibit further elaboration of existing transformation-related properties (1,13,14). Isolating cells after growth in agar, co-expressing additional oncogenes or reisolating transformed cells after tumor formation in nude mice (13–15) can accelerate this process. Substraction hybridization of a cDNA library generated from a mutant Ad5 (H5ts125)-transformed rat embryo cell clone that forms small, slow-growing and compact tumors, E11 (1,13,14), from a cDNA library produced from a highly aggressive tumorigenic nude mouse tumor-derived E11 clone, E11-MT (2,14), resulted in the identification and cloning of PEG-3 (3). Elevated PEG-3 expression occurs in progressed H5ts125-transformed clones and in normal rat embryo fibroblast (CREF) (16) cells displaying a tumorigenic phenotype as a result of expression of diverse acting oncogenes, including Ha-ras, V-src, human papilloma virus type-18 transforming genes and a specific mutant of Ad5 (H5 hr1) (3). When PEG-3 is ectopically expressed in E11 cells, anchorage-independence, an in vitro marker of progression in this model system, is increased (3). These results indicate that PEG-3 can directly contribute to expression of the in vitro transformed phenotype in H5ts125-transformed rat embryo cells.

A number of questions remain concerning the potential role of PEG-3 in regulating the cancer phenotype. These include the biological consequence of elevating PEG-3 expression in normal cells and in vivo outcome of modifying PEG-3 expression in cancer cells. In the present study we demonstrate that PEG-3 lacks classical oncogenic potential, but overexpression of this gene in rodent or human tumor cells results in aggressive tumorigenic properties in athymic nude mice. The phenotypic changes induced by over expression of PEG-3 correlate with an increase in VEGF production. These findings provide a potential mechanistic framework by which PEG-3 enhances the in vivo cancer phenotype to tumor cells.

Figure 1:
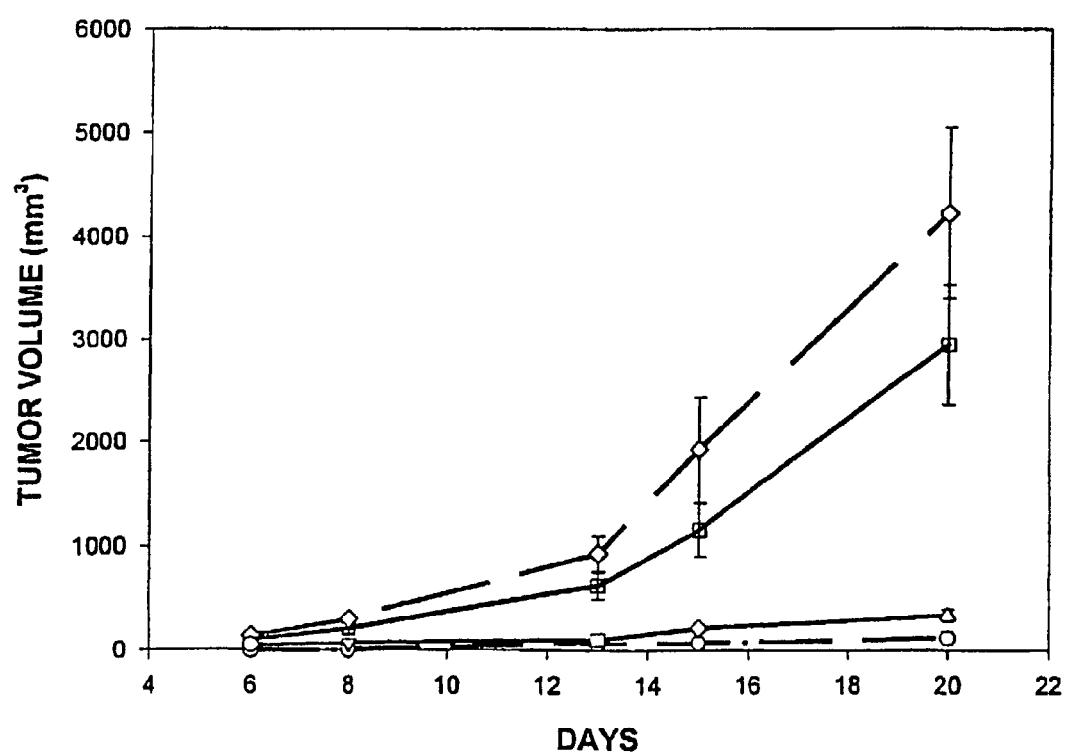
FIG. 1

Effect of PEG-3 expression on oncogenic potential of E11 and E11-NMT cells. Athymic nude mice were injected subcutaneously with $1 \times 10^6$ E11 (open circles), E11-NMT (open squares), E11/PEG-3 S cl 13 (open diamonds) or E11-NMT/PEG-3AScl3 (open triangles). Mice were evaluated daily until palpable tumors were observed and tumor volumes were measured at day 20.

FIG. 2

Photograph comparing tumor growth of E11 and its derivates in nude mice. Pictures taken 20 days post-injection with the indicated cell type.

FIG. 3

Gene expression and VEGF protein levels as a consequence of PEG-3 expression. (A) Northern blotting analysis of steady-state PEG-3, VEGF, Ad5 E1A and GAPDH RNA in E11 and its variants. (B) VEGF protein secretion. Equal numbers of cells were cultured for 36 hr in medium without serum, the medium was collected, concentrated and VEGF protein levels were determined by Western blotting using a VEGF monoclinal antibody and the ECL approach. Lane designations: 1:E11-NMT; 2:E11-NMT/PEG-3AScl3; 3:E11; and 4:E11/PEG-3Scl13.

FIG. 4

Ectopic expression of PEG-3 in T98G and DU-145 tumor cells facilitates tumor formation in vivo in nude mice. (A)Ectopic expression of the rat PEG-3 gene in the low tumorigenic human glioblastoma multiform cell line T98G induces a progressive tumorigenic phenotype. Pooled cultures of vector or rat PEG-3 cDNA transfected Zeocin resistant T98G cells were injected into 4 athymic nude mice/group. Animals were followed weekly until palpable tumors were observed. No tumors developed in vector transfected T98G cells by 5 months at which time the experiment as terminated. (B)Ectopic expression of rat PEG-3 in DU-145 cells induces an aggressive oncogenic phenotype. DU-145 cells ere infected with 100 pfu/cell of Ad.PEG-3 S or Ad.Vec (Null, replication incompetent Ad lacking the PEG-3 gene)and 48 hr later the cells were mixed with Matrigel and injected subcutaneously into athymic nude mice (4 animals/group). Animals were monitored as above and tumor volume was determined after 1 month. (*)indicated statistically significant difference of $p<0.025$.

FIG. 5

Representative histopathology of formalin-fixed paraffin-embedded tumors. Serial sections were stained with either hematoxylin-eosin (panels A,C,E,G) or immunostained with antibody to the endothelial marker, CD31 (panels B,D,F,H). Legend: E11:A,B; E11-NMT:C,D; E11/PEG-3Scl 13:E,F; E11/NMT/PEG-3AScl3:G,H.Original magnification, ×200.

FIG. 6

Nuclear run-on analysis of transcription of the PEG-3, Ad5E1A, bFGF, VEGF, PTN, MK, GAPDH and pBR322 genes in E11, E11-NMT, E11/PEG-3S and E11-NMT/PEG-3AS cells.

FIG. 7

The activity of a VEGF-promoter-luciferase construct is enhanced in PEG-3 expressing rodent cells. The different cell types were transfected with the pGL3/VEGF vector and a pSV-beta-galactosidase vector and luciferase and beta-gal activities were determined. Results are from three independent experiments with triplicate samples per experiment and reflect average fold-increase in luciferase activity(relative to E11 which represents 1)±standard error.

FIG. 8

Transfection of PEG-3 into E11 cells induces steady-state VEGF mRNA. E11 cells were transfected with a pZeoSV/PEG-3 or pZeo SV vector, 4 hr later replicate cultures received cycloheximide and 30 hr later total RNA was extracted and analyzed by Northern blotting for PEG-3, VEGF, Ad5 E1A and GAPDH mRNA expression.

DETAILED DESCRIPTION OF THE INVENTION

The present invention provides a method for identifying a gene which is expressed at a modulated level in an aggressive cancer which comprises: (a) measuring baseline expression levels of genes in cancer cells; (b) introducing into the cancer cells an expression vector which directs expression of rat PEG-3; (c) measuring the expression levels of genes in the cells from step (b); and (d) identifying genes, the expression of which is modulated in an aggressive cancer.

In an embodiment of this invention the measurement of expression levels of genes in step (a) and/or step (c) comprises measuring mRNA levels. In yet another embodiment the measurement of expression levels of genes in step (a) and/or step (c) comprises measuring RNA levels.

In another embodiment the genes identified in step (d) are used for diagnosing whether a subject suffers from an aggressive form of cancer.

Definitions

As used herein "therapeutic gene" means DNA encoding an amino acid sequence corresponding to a functional protein capable of exerting a therapeutic effect on cancer cells or having a regulatory effect on the expression of a gene which functions in cells.

As used herein "nucleic acid molecule" includes both DNA and RNA and, unless otherwise specified, includes both double-stranded and single-stranded nucleic acids. Also included are hybrids such as DNA-RNA hybrids. Reference to a nucleic acid sequence can also include modified bases as long as the modification does not significantly interfere either with binding of a ligand such as a protein by the nucleic acid or Watson-Crick base pairing.

As used herein "enhancer element" is a nucleotide sequence that increases the rate of transcription of the therapeutic genes or genes of interest but does not have promoter activity. An enhancer can be moved upstream, downstream, and to the other side of a promoter without significant loss of activity.

Two DNA or polypeptide sequences are "substantially homologous" when at least about 80% (preferably at least about 90%, and most preferably at least about 95%–99%) of the nucleotides or amino acids match over a defined length of the molecule. As used herein, "substantially homologous" also refers to sequences showing identity (100% identical sequence) to the specified DNA or polypeptide sequence. DNA sequences that are substantially homologous can be identified in a Southern hybridization, experiment under, for example, stringent conditions, as defined for that particular system. Defining appropriate hybridization conditions is within the skill of the art. See, e.g., Sambrook et al., supra; DNA Cloning, vols I & II, supra; Nucleic Acid Hybridization, supra.

A sequence "functionally equivalent" to a PEG-3 promoter sequence is one which functions in the same manner as the PEG-3 promoter sequence. Thus, a promoter sequence "functionally equivalent" to the PEG-3 promoter described herein is one which is capable of directing transcription of a downstream coding sequence in substantially similar timeframes of expression and in substantially similar amounts and with substantially similar tissue specificity as the PEG-3 promoter sequence.

A DNA "coding sequence" or a "nucleotide sequence encoding" a particular protein, is a DNA sequence which is transcribed and translated into a polypeptide in vivo or in vitro when placed under the control of appropriate regulatory sequences. The boundaries of the coding sequence are determined by a start codon at the 5'-(amino) terminus and a translation stop codon at the 3'-(carboxy) terminus. A coding sequence can include, but is not limited to, procaryotic sequences, cDNA from eucaryotic mRNA, genomic DNA sequences from eucaryotic (e.g., mammalian) sources, viral RNA or DNA, and even synthetic nucleotide sequences. A transcription termination sequence will usually be located 3' to the coding sequence.

DNA "control sequences" refers collectively to promoter sequences, polyadenylation signals, transcription termination sequences, upstream regulatory domains, enhancers, and the like, untranslated regions, including 5'-UTRs (untranslated regions) and 3'-UTRs, which collectively provide for the transcription and translation of a coding sequence in a host cell.

"Operably linked" refers to an arrangement of nucleotide sequence elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

A control sequence "directs the transcription" of a coding sequence in a cell when RNA polymerase will bind the promoter sequence and transcribe the coding sequence into mRNA, which is then translated into the polypeptide encoded by the coding sequence.

A cell has been "transformed" by exogenous DNA when such exogenous DNA has been introduced inside the cell membrane. Exogenous DNA may or may not be integrated (covalently linked) into chromosomal DNA making up the genome of the cell. In procaryotes and yeasts, for example, the exogenous DNA may be maintained on an episomal element, such as a plasmid. In eucaryotic cells, a stably transformed cell is generally one in which the exogenous DNA has become integrated into the chromosome so that it is inherited by daughter cells through chromosome replication, or one which includes stably maintained extrachromosomal plasmids. This stability is demonstrated by the ability of the eucaryotic cell to establish cell lines or clones comprised of a population of daughter cells containing the exogenous DNA.

A "heterologous" region of a DNA construct is an identifiable segment of DNA within or attached to another DNA molecule that is not found in association with the other molecule in nature. For example, a sequence encoding a protein other than a PEG-3 protein is considered a heterologous sequence when linked to a PEG-3 promoter. Another example of a heterologous coding sequence is a construct where the coding sequence itself is not found in nature (e.g., synthetic sequences having codons different from the native gene). Likewise, a chimeric sequence, comprising a heterologous gene linked to a PEG-3 promoter, will be considered heterologous since such chimeric constructs are not-normally found in nature. Allelic variation or naturally occurring mutational events do not give rise to a heterologous region of DNA, as used herein.

Vectors

Especially preferred are virus based vectors. In the case of eukaryotic cells, retrovirus or adenovirus based vectors are preferred. Such vectors contain all or a part of a viral genome, such as long term repeats ("LTRs"), promoters (e.g., CMV promoters, SV40 promoter, RSV promoter), enhancers, and so forth. When the host cell is a prokaryote, bacterial viruses, or phages, are preferred. Exemplary of such vectors are vectors based upon, e.g., lambda phage. In any case, the vector may comprise elements of more than one virus.

The resulting vectors are transfected or transformed into a host cell, which may be eukaryotic or prokaryotic.

The gene transfer vector of the present invention may additionally comprise a gene encoding a marker or reporter molecule to more easily trace expression of the vector.

The particular reporter molecule which can be employed in the present invention is not critical thereto. Examples of such reporter molecules which can be employed in the present invention are well-known in the art and include beta-galactosidase (Fowler et al, Proc. Natl. Acad. Sci., USA, 74:1507 (1977)), luciferase (Tu et al, Biochem., 14:1970 (1975)), and chloramphenicol acetyltransferase (Gorman et al, Mol. Cell Biol., 2:1044–1051 (1982)).

The gene transfer vector may contain more than one gene encoding the same or different foreign polypeptides or RNAs.

The gene transfer vector may be any construct which is able to replicate within a host cell and includes plasmids, DNA viruses, retroviruses, as well as isolated nucleotide molecules. Liposome-mediated transfer of the gene transfer vector may also be carried out in the present invention.

Examples of such plasmids which can be employed in the present invention include pGL3-based plasmids (Promega™) An example of such DNA viruses which can be employed in the present invention are adenoviruses.

Adenoviruses have attracted increasing attention as expression vectors, especially for human gene therapy (Berkner, Curr. Top. Microbiol. Immunol., 158:39–66 (1992)).

Examples of such adenovirus serotypes which can be employed in the present invention are well-known in the art and include more than 40 different human adenoviruses, e.g., Ad12 (subgenus A), Ad3 and Ad7 (Subgenus B), Ad2 and Ad5 (Subgenus C), Ad8 (Subgenus D), Ad4 (Subgenus E), Ad40 (Subgenus F) (Wigand et al, In: Adenovirus DNA, Doerfler, Ed., Martinus Nijhoff Publishing, Boston, pp. 408–441 (1986)). Ad5 of subgroup C is the preferred adenovirus employed in the present invention. This is because Ad5 is a human adenovirus about which a great deal of biochemical and genetic information is known, and it has historically been used for most constructions employing adenovirus as a vector. Also, adenoviral vectors are commercially available, e.g., pCA3 (Microbix Biosystems Inc.).

Methods for producing adenovirus vectors are well-known in the art (Berkner et al, Nucleic Acids Res., 11:6003–6020 (1983); van Doren et al, Mol. Cell. Biol., 4:1653–1656 (1984); Ghosh-Choudhury et al, Biochem. Biophys. Res. Commun., 147:964–973 (1987); McGrory et al, Virol., 163:614–617 (1988); and Gluzman et al, In: Eurkaryotic Viral Vectors, Ed. Gluzman, Y. pages 187–192, Cold Spring Harbor Laboratory (1982)).

Derivative Nucleic Acid Molecules

Derivative molecules would retain the functional property of the PEG-3 promoter, namely, the molecule having such substitutions will still permit the tissue specific expression of the gene of interest. Modification is permitted so long as the derivative molecules retain its increased potency compared to PEG-3 promoter alone and its tissue specificity.

Examples of therapeutic genes include suicide genes. These are genes sequences the expression of which produces a protein or agent that inhibits melanoma tumor cell growth or induces melanoma tumor cell death. Suicide genes include genes encoding enzymes, oncogenes, tumor suppressor genes, genes encoding toxins, genes encoding cytokines, or a gene encoding oncostatin. The purpose of the therapeutic gene is to inhibit the growth of or kill skin cancer cells or produce cytokines or other cytotoxic agents which directly or indirectly inhibit the growth of or kill the cancer cell.

Suitable enzymes include thymidine kinase (TK), xanthine-guanine phosphoribosyltransferase (GPT) gene from *E. coli* or *E. coli* cytosine deaminase (CD), or hypoxanthine phosphoribosyl transferase (HPRT).

Suitable oncogenes and tumor suppressor genes include neu, EGF, ras (including H, K, and N ras), p53, Retinoblastoma tumor suppressor gene (Rb), Wilm's Tumor Gene Product, Phosphotyrosine Phosphatase (PTPase), and nm23. Suitable toxins include *Pseudomonas* exotoxin A and S; diphtheria toxin (DT); *E. coli* LT toxins, Shiga toxin, Shiga-like toxins (SLT-1, -2), ricin, abrin, supporin, and gelonin.

Suitable cytokines include interferons, GM-CSF interleukins, tumor necrosis factor (TNF) (Wong G, et al., Human GM-CSF: Molecular cloning of the complementary DNA and purification of the natural and recombinant proteins. Science 1985; 228:810); WO9323034 (1993); Horisberger M. A., et al., Cloning and sequence analyses of cDNAs for interferon-beta and virus-induced human Mx proteins reveal that they contain putative guanine nucleotide-binding sites: functional study of the corresponding gene promoter. Journal of Virology, 1990 March, 64(3):1171–81; Li Y P et al., Proinflammatory cytokines tumor necrosis factor-alpha and IL-6, but not IL-1, down-regulate the osteocalcin gene promoter. Journal of Immunology, Feb. 1, 1992, 148(3): 788–94; Pizarro T. T., et al. Induction of TNF alpha and TNF beta gene expression in rat cardiac transplants during allograft rejection. Transplantation, 1993 August, 56(2): 399–404). (Breviario F., et al., Interleukin-1-inducible genes in endothelial cells. Cloning of a new gene related to C-reactive protein and serum amyloid P component. Journal of Biological Chemistry, Nov. 5, 1992, 267(31):22190–7; Espinoza-Delgado I., et al., Regulation of IL-2 receptor subunit genes in human monocytes. Differential effects of IL-2 and IFN-gamma. Journal of Immunology, Nov. 1, 1992, 149(9):2961–8; Algate P. A., et al., Regulation of the interleukin-3 (IL-3) receptor by IL-3 in the fetal liver-derived FL5.12 cell line. Blood, 1994 May 1, 83(9):2459–68; Cluitmans F. H., et al., IL-4 down-regulates IL-2-, IL-3-, and GM-CSF-induced cytokine gene expression in peripheral blood monocytes. Annals of Hematology, 1994 June, 68(6): 293–8; Lagoo, A. S., et al., IL-2, IL-4, and IFN-gamma gene expression versus secretion in superantigen-activated T cells. Distinct requirement for costimulatory signals through adhesion molecules. Journal of Immunology, Feb. 15, 1994, 152(4):1641–52; Martinez 0. M., et al., IL-2 and IL-5 gene expression in response to alloantigen in liver allograft recipients and in vitro. Transplantation, 1993 May, 55(5):1159–66; Pang G, et al., GM-CSF, IL-1 alpha, IL-1 beta, IL-6, IL-8, IL-10, ICAM-1 and VCAM-1 gene expression and cytokine production in human duodenal fibroblasts stimulated with lipopolysaccharide, IL-1 alpha and TNF-alpha. Clinical and Experimental Immunology, 1994 June, 96(3):437–43; Ulich T. R., et al., Endotoxin-induced cytokine gene expression in vivo. III. IL-6 mRNA and serum protein expression and the in vivo hematologic effects of IL-6. Journal of Immunology, Apr. 1, 1991, 146(7):2316–23; Mauviel A., et al., Leukoregulin, a T cell-derived cytokine, induces IL-8 gene expression and secretion in human skin fibroblasts. Demonstration and secretion in human skin fibroblasts. Demonstration of enhanced NF-kappa B binding and NF-kappa B-driven promoter activity. Journal of Immunology, Nov. 1, 1992, 149(9):2969–76).

Growth factors include Transforming Growth Factor-.alpha. (TGF-alpha) and beta (TGF-beta), cytokine colony stimulating factors (Shimane M., et al., Molecular cloning and characterization of G-CSF induced gene cDNA. Biochemical and Biophysical Research Communications, Feb. 28, 1994, 199(1):26–32; Kay A. B., et al., Messenger RNA expression of the cytokine gene cluster, interleukin 3 (IL-3), IL-4, IL-5, and granulocyte/macrophage colony-stimulating factor, in allergen-induced late-phase cutaneous reactions in atopic subjects. Journal of Experimental Medicine, Mar. 1, 1991, 173(3):775–8; de Wit H, et al., Differential regulation of M-CSF and IL-6 gene expression in monocytic cells. British Journal of Haematology, 1994 February, 86(2):259–64; Sprecher E., et al., Detection of IL-1 beta, TNF-alpha, and IL-6 gene transcription by the polymerase chain reaction in keratinocytes, Langerhans cells and peritoneal exudate cells during infection with herpes simplex virus-1. Archives of Virology, 1992, 126(1–4):253–69).

Preferred vectors for use in the methods of the present invention are viral including adenoviruses, retroviral, vectors, adeno-associated viral (AAV) vectors.

The viral vector selected should meet the following criteria: 1) the vector must be able to infect the tumor cells and thus viral vectors having an appropriate host range must be selected; 2) the transferred gene should be capable of persisting and being expressed in a cell for an extended period of time; and 3) the vector should be safe to the host and cause minimal cell transformation. Retroviral vectors and adenoviruses offer an efficient, useful, and presently the best-characterized means of introducing and expressing foreign genes efficiently in mammalian cells. These vectors have very broad host and cell type ranges, express genes stably and efficiently. The safety of these vectors has been proved by many research groups. In fact many are in clinical trials.

Other virus vectors that may be used for gene transfer into cells for correction of disorders include retroviruses such as Moloney murine leukemia virus (MoMuLV); papovaviruses such as JC, SV40, polyoma, adenoviruses; Epstein-Barr Virus (EBV); papilloma viruses, e.g. bovine papilloma virus type I (BPV); vaccinia and poliovirus and other human and animal viruses.

Adenoviruses have several properties that make them attractive as cloning vehicles (Bachettis et al.: Transfer of gene for thymidine kinase-deficient human cells by purified herpes simplex viral DNA. PNAS USA, 1977 74:1590; Berkner, K. L.: Development of adenovirus vectors for expression of heterologous genes. Biotechniques, 1988 6:616; Ghosh-Choudhury G., et al., Human adenovirus cloning vectors based on infectious bacterial plasmids. Gene 1986; 50:161; Hag-Ahmand Y., et al., Development of a helper-independent human adenovirus vector and its use in the transfer of the herpes simplex virus thymidine kinase gene. J Virol 1986; 57:257; Rosenfeld M., et al., Adenovirus-mediated transfer of a recombinant alpha..sub.1-antitrypsin gene to the lung epithelium in vivo. Science 1991; 252:431).

For example, adenoviruses possess an intermediate sized genome that replicates in cellular nuclei; many serotypes are clinically innocuous; adenovirus genomes appear to be stable despite insertion of foreign genes; foreign genes appear to be maintained without loss or rearrangement; and adenoviruses can be used as high level transient expression vectors with an expression period up to 4 weeks to several months. Extensive biochemical and genetic studies suggest that it is possible to substitute up to 7–7.5 kb of heterologous sequences for native adenovirus sequences generating viable, conditional, helper-independent vectors (Kaufman R. J.; identification of the component necessary for adenovirus translational control and their utilization in cDNA expression vectors. PNAS USA, 1985 82:689).

AAV is a small human parvovirus with a single stranded DNA genome of approximately 5 kb. This virus can be propagated as an integrated provirus in several human cell types. AAV vectors have several advantage for human gene therapy. For example, they are trophic for human cells but can also infect other mammalian cells; (2) no disease has been associated with AAV in humans or other animals; (3) integrated AAV genomes appear stable in their host cells; (4) there is no evidence that integration of AAV alters expression of host genes or promoters or promotes their rearrangement; (5) introduced genes can be rescued from the host cell by infection with a helper virus such as adenovirus.

HSV-1 vector system facilitates introduction of virtually any gene into non-mitotic cells (Geller et al. an efficient deletion mutant packaging system for a defective herpes simplex virus vectors: Potential applications to human gene therapy and neuronal physiology. PNAS USA, 1990 87:8950).

Another vector for mammalian gene transfer is the bovine papilloma virus-based vector (Sarver N, et al., Bovine papilloma virus DNA: A novel eukaryotic cloning vector. Mol Cell Biol 1981; 1:486).

Vaccinia and other poxvirus-based vectors provide a mammalian gene transfer system. Vaccinia virus is a large double-stranded DNA virus of 120 kilodaltons (kd) genomic size (Panicali D, et al., Construction of poxvirus as cloning vectors: Insertion of the thymidine kinase gene from herpes simplex virus into the DNA of infectious vaccine virus. Proc Natl Acad Sci USA 1982; 79:4927; Smith et al. infectious vaccinia virus recombinants that express hepatitis B virus surface antigens. Nature, 1983 302:490.)

Retroviruses are packages designed to insert viral genes into host cells (Guild B, et al., Development of retrovirus vectors useful for expressing genes in cultured murine embryonic cells and hematopoietic cells in vivo. J Virol 1988; 62:795; Hock R. A., et al., Retrovirus mediated transfer and expression of drug resistance genes in human hemopoietic progenitor cells. Nature 1986; 320:275).

The basic retrovirus consists of two identical strands of RNA packaged in a proviral protein. The core surrounded by a protective coat called the envelope, which is derived from the membrane of the previous host but modified with glycoproteins contributed by the virus.

Markers and amplifiers can also be employed in the subject expression systems. A variety of markers are known which are useful in selecting for transformed cell lines and generally comprise a gene whose expression confers a selectable phenotype on transformed cells when the cells are grown in an appropriate selective medium. Such markers for mammalian cell lines include, for example, the bacterial xanthine-guanine phosporibosyl transferase gene, which can be selected for in medium containing mycophenolic acid and xanthine (Mulligan et al. (1981) Proc. Natl. Acad. Sci. USA 78:2072–2076), and the aminoglycoside phosphotransferase gene (specifying a protein that inactivates the antibacterial action of neomycin/kanamycin derivatives), which can be selected for using medium containing neomycin derivatives such as G418 which are normally toxic to mammalian cells (Colbere-Garapin et al. (1981) J. Mol. Biol. 150:1–14). Useful markers for other eucaryotic expression systems, are well known to those of skill in the art.

Infection can be carried out in vitro or in vivo. In vitro infection of cells is performed by adding the gene transfer vectors to the cell culture medium. When infection is carried out in vivo, the solution containing the gene transfer vectors may be administered by a variety of modes, depending on the tissue which is to be infected. Examples of such modes of administration include injection of gene transfer vectors into the skin, topical application onto the skin, direct application to a surface of epithelium, or instillation into an organ (e.g., time release patch or capsule below the skin or into a tumor).

Expression can be amplified by placing an amplifiable gene, such as the mouse dihydrofolate reductase (dhfr) gene adjacent to the coding sequence. Cells can then be selected for methotrexate resistance in dhfr-deficient cells. See, e.g. Urlaub et al. (1980) Proc. Natl. Acad. Sci. USA 77:4216–4220; Rungold et al. (1981) J. Mol. and Appl. Genet. 1:165–175.

The above-described system can be used to direct the expression of a wide variety of procaryotic, eucaryotic and viral proteins, including, for example, viral glycoproteins suitable for use as vaccine antigens, immunomodulators for regulation of the immune response, hormones, cytokines and growth factors, as well as proteins useful in the production of other biopharmaceuticals.

It may also be desirable to produce mutants or analogs of the proteins of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; DNA Cloning, Vols. I and II, supra; Nucleic Acid Hybridization, supra.

For purposes of the present invention, it is particularly desirable to further engineer the coding sequence to effect secretion of the polypeptide from the host organism. This enhances clone stability and prevents the toxic build up of proteins in the host cell so that expression can proceed more efficiently. Homologous signal sequences can be used for this purpose with proteins normally found in association with a signal sequence. Additionally, heterologous leader sequences which provide for secretion of the protein can be added to the constructs. Preferably, processing sites will be included such that the leader fragment can be cleaved from the protein expressed therewith. (See, e.g., U.S. Pat. No. 4,336,246 for a discussion of how such cleavage sites can be introduced). The leader sequence fragment typically encodes a signal peptide comprised of hydrophobic amino acids.

In one embodiment of the invention, a heterologous gene sequence, i.e., a therapeutic gene, is inserted into the nucleic acid molecule of the invention. Other embodiments of the isolated nucleic acid molecule of the invention include the addition of a single enhancer element or multiple enhancer elements which amplify the expression of the heterologous therapeutic gene without compromising tissue specificity.

The transformation procedure used depends upon the host to be transformed. Mammalian cells can conveniently be transformed using, for example, DEAE-dextran based procedures, calcium phosphate precipitation (Graham, F. L. and Van der Eb, A. J. (1973) Virology 52:456–467), protoplast fusion, liposome-mediated transfer, polybrene-mediated transfection and direct microinjection of the DNA into nuclei. Bacterial cells will generally be transformed using calcium chloride, either alone or in combination with other divalent cations and DMSO (Sambrook, Fritsch & Maniatis, Molecular Cloning: A Laboratory Manual, Second Edition (1989)). DNA can also be introduced into bacterial cells by electroporation. Methods of introducing exogenous DNA into yeast hosts typically include either the transformation of spheroplasts or transformation of intact yeast cells treated with alkali cations.

The constructs can also be used in gene therapy or nucleic acid immunization, to direct the production of the desired gene product in vivo, by administering the expression constructs directly to a subject for the in vivo translation thereof. See, e.g. EPA Publication No. 336,523 (Dreano et al., published Oct. 11, 1989). Alternatively, gene transfer can be accomplished by transfecting the subject's cells or tissues with the expression constructs ex vivo and reintroducing the transformed material into the host. The constructs can be directly introduced into the host organism, i.e., by injection (see International Publication No. WO/90/11092; and Wolff et al., (1990) Science 247:1465–1468). Liposome-mediated gene transfer can also be accomplished using known methods. See, e.g., Hazinski et al., (1991) Am. J. Respir. Cell Mol. Biol. 4:206–209; Brigham et al. (1989) Am. J. Med. Sci. 298:278–281; Canonico et al. (1991) Clin. Res. 39:219A; and Nabel et al. (1990) Science 249:1285–1288. Targeting agents, such as antibodies directed against surface antigens expressed on specific cell types, can be covalently conjugated to the liposomal surface so that the nucleic acid can be delivered to specific tissues and cells for local administration.

Human Gene Therapy and Diagnostic Use of Vector

There are several protocols for human gene therapy which have been approved for use by the Recombinant DNA Advisory Committee (RAC) which conform to a general protocol of target cell infection and administration of transfected cells (see for example, Blaese, R. M., et al., 1990; Anderson, W. F., 1992; Culver, K. W. et al., 1991). In addition, U.S. Pat. No. 5,399,346 (Anderson, W. F. et al., Mar. 21, 1995, U.S. Ser. No. 220,175) describes procedures for retroviral gene transfer. The contents of these support references are incorporated in their entirety into the subject application. Retroviral-mediated gene transfer requires target cells which are undergoing cell division in order to achieve stable integration hence, cells are collected from a subject often by removing blood or bone marrow. It may be necessary to select for a particular subpopulation of the originally harvested cells for use in the infection protocol. Then, a retroviral vector containing the gene(s) of interest would be mixed into the culture medium. The vector binds to the surface of the subject's cells, enters the cells and inserts the gene of interest randomly into a chromosome. The gene of interest is now stably integrated and will remain in place and be passed to all of the daughter cells as the cells grow in number. The cells may be expanded in culture for a total of 9–10 days before reinfusion (Culver et al., 1991). As the length of time the target cells are left in culture increases, the possibility of contamination also increases, therefore a shorter protocol would be more beneficial.

This invention provides for the construction of retrovirus vectors containing the PEG-3 promoter or a functional equivalent thereof linked to a gene of interest for use in gene therapy or for diagnostic uses. The efficiency of transduction of these vectors can be tested in cell culture systems.

Uses of the Compositions of the Invention

This invention involves targeting a gene-of-interest to the a cancer cell so that the protein encoded by the gene is expressed and directly or indirectly ameliorate the diseased state. Since the PEG-3 promoter is specifically active in a cancer cell which is undergoing cancer progression, it will act as a tissue specific promoter (specific for cancer cells).

After infecting a susceptible cell, the transgene driven by a specific promoter in the vector expresses the protein encoded by the gene. The use of the highly specific gene vector will allow selective expression of the specific genes in cancer cells.

The basic tasks in the present method of the invention are isolating the gene of interest, selecting the proper vector vehicle to deliver the gene of interest to the body, administering the vector having the gene of interest into the body, and achieving appropriate expression of the gene of interest. The present invention provides packaging the cloned genes, i.e. the genes of interest, in such a way that they can be injected directly into the bloodstream or relevant organs of patients who need them. The packaging will protect the foreign DNA from elimination by the immune system and direct it to appropriate tissues or cells.

In one embodiment of the invention, the gene of interest (desired coding sequence) is a tumor suppressor gene. The tumor suppressor gene may be p21, RB (retinoblastoma) or p53. One of skill in the art would know of other tumor suppressor genes. Recent U.S. Pat. Nos. 6,025,127 and 5,912,236 are hereby incorporated by reference to more explicitly describe the state of the art as to tumor suppressor genes.

Along with the human or animal gene of interest another gene, e.g., a selectable marker, can be inserted that will allow easy identification of cells that have incorporated the modified retrovirus. The critical focus on the process of gene therapy is that the new gene must be expressed in target cells at an appropriate level with a satisfactory duration of expression.

The methods described below to modify vectors and administering such modified vectors into the skin are merely for purposes of illustration and are typical of those that might be used. However, other procedures may also be employed, as is understood in the art.

Most of the techniques used to construct vectors and the like are widely practiced in the art, and most practitioners are familiar with the standard resource materials which describe specific conditions and procedures. However, for convenience, the following paragraphs may serve as a guideline.

General Methods for Vector Construction

Construction of suitable vectors containing the desired therapeutic gene coding and control sequences employs standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides are cleaved, tailored, and religated in the form desired.

Site-specific DNA cleavage is performed by treating with the suitable restriction enzyme (or enzymes) under conditions which are generally understood in the art, and the particulars of which are specified by the manufacturer of these commercially available restriction enzymes (See, e.g. New England Biolabs Product Catalog). In general, about 1 μg of plasmid or DNA sequences is cleaved by one unit of enzyme in about 20 μl of buffer solution. Typically, an excess of restriction enzyme is used to insure complete digestion of the DNA substrate.

Incubation times of about one hour to two hours at about 37 degree. C. are workable, although variations can be tolerated.

After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in Methods in Enzymology 65:499–560 (1980).

Restriction cleaved fragments may be blunt ended by treating with the large fragment of E. coli DNA polymerase I (Klenow) in the presence of the four deoxynucleotide triphosphates (dNTPs) using incubation times of about 15 to 25 min at 20.degree. C. to 25.degree. C. in 50 mM Tris (pH 7.6) 50 mM NaCl, 6 mM MgCl.sub.2, 6 mM DTT and 5–10 .mu.M dNTPs. The Klenow fragment fills in at 5' sticky ends but chews back protruding 3' single strands, even though the four dNTPs are present. If desired, selective repair can be performed by supplying only one of the dNTPs, or with selected dNTPs, within the limitations dictated by the nature of the sticky ends. After treatment with Klenow, the mixture is extracted with phenol/chloroform and ethanol precipitated. Treatment under appropriate conditions with Sl nuclease or Bal-31 results in hydrolysis of any single-stranded portion.

Ligations are performed in 10–50 $\mu$l volumes under the following standard conditions and temperatures using T4 DNA ligase. Ligation protocols are standard (D. Goeddel (ed.) Gene Expression Technology: Methods in Enzymology (1991)). In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Alternatively, religation can be prevented in vectors which have been double digested by additional restriction enzyme digestion of the unwanted fragments.

Suitable vectors include viral vector systems e.g. ADV, RV, and AAV (R. J. Kaufman "Vectors used for expression in mammalian cells" in Gene Expression Technology, edited by D. V. Goeddel (1991).

Many methods for inserting functional DNA transgenes into cells are known in the art. For example, non-vector methods include nonviral physical transfection of DNA into cells; for example, microinjection (DePamphilis et al., Bio-Technique 6:662–680 (1988)); liposomal mediated transfection (Felgner et al., Proc. Natl. Acad. Sci. USA, 84:7413–7417 (1987), Felgner and Holm, Focus 11:21–25 (1989) and Felgner et al., Proc. West. Pharmacol. Soc. 32: 115–121 (1989)) and other methods known in the art.

Administration of Modified Vectors into Subject

One way to get DNA into a target cell is to put it inside a membrane bound sac or vesicle such as a spheroplast or liposome, or by calcium phosphate precipitation (CaPO.sub.4) (Graham F. and Van der Eb, A., Virology 52:456 1973; Schaefer-Ridder M., et al., Liposomes as gene carriers: Efficient transduction of mouse L cells by thymidine kinase gene. Science 1982; 215:166; Stavridis J. C., et al., Construction of transferrin-coated liposomes for in vivo transport of exogenous DNA to bone marrow erythroblasts in rabbits. Exp Cell Res 1986; 164:568–572).

A vesicle can be constructed in such a way that its membrane will fuse with the outer membrane of a target cell. The vector of the invention in vesicles can home into the cancer cells.

The spheroplasts are maintained in high ionic strength buffer until they can be fused through the mammalian target cell using fusogens such as polyethylene glycol.

Liposomes are artificial phospholipid vesicles. Vesicles range in size from 0.2 to 4.0 micrometers and can entrap 10% to 40% of an aqueous buffer containing macromolecules. The liposomes protect the DNA from nucleases and facilitate its introduction into target cells. Transfection can also occur through electroporation.

Before administration, the modified vectors are suspended in complete PBS at a selected density for injection. In addition to PBS, any osmotically balanced solution which is physiologically compatible with the subject may be used to suspend and inject the modified vectors into the host.

For injection, the cell suspension is drawn up into the syringe and administered to anesthetized recipients. Multiple injections may be made using this procedure. The viral suspension procedure thus permits administration of genetically modified vectors to any predetermined site in the skin, is relatively non-traumatic, allows multiple administrations simultaneously in several different sites or the same site using the same viral suspension. Multiple injections may consist of a mixture of therapeutic genes.

Survival of the Modified Vectors so Administered

Expression of a gene is controlled at the transcription, translation or post-translation levels. Transcription initiation is an early and critical event in gene expression. This depends on the promoter and enhancer sequences and is influenced by specific cellular factors that interact with these sequences. The transcriptional unit of many prokaryotic genes consists of the promoter and in some cases enhancer or regulator elements (Banerji et al., Cell 27:299 (1981); Corden et al., Science 209:1406 (1980); and Breathnach and Chambon, Ann. Rev. Biochem. 50:349 (1981)).

For retroviruses, control elements involved in the replication of the retroviral genome reside in the long terminal repeat (LTR) (Weiss et al., eds., In: The molecular biology of tumor viruses: RNA tumor viruses, Cold Spring Harbor Laboratory, Cold Spring Harbor, N.Y. (1982)).

Moloney murine leukemia virus (MLV) and Rous sarcoma virus (RSV) LTRs contain promoter and enhancer sequences (Jolly et al., Nucleic Acids Res. 11:1855 (1983); Capecchi et al., In: Enhancer and eukaryotic gene expression, Gulzman and Shenk, eds., pp. 101–102, Cold Spring Harbor Laboratories, Cold Spring Harbor, N.Y.).

Promoter and enhancer regions of a number of non-viral promoters have also been described (Schmidt et al., Nature 314:285 (1985); Rossi and de Crombrugghe, Proc. Natl. Acad. Sci. USA 84:5590–5594 (1987)).

In addition to using viral and non-viral promoters to drive therapeutic gene expression, an enhancer sequence may be used to increase the level of therapeutic gene expression. Enhancers can increase the transcriptional activity not only of their native gene but also of some foreign genes (Armelor, Proc. Natl. Acad. Sci. USA 70:2702 (1973)).

Therapeutic gene expression may also be increased for long term stable expression after injection using cytokines to modulate promoter activity.

The methods of the invention are exemplified by preferred embodiments in which modified vectors carrying a therapeutic gene are injected intracerebrally into a subject.

The most effective mode of administration and dosage regimen for the molecules of the present invention depends upon the exact location of the cancer being treated, the severity and course of the cancer, the subject's health and response to treatment and the judgment of the treating physician. Accordingly, the dosages of the molecules should be titrated to the individual subject. The molecules may be delivered directly or indirectly via another cell, autologous cells are preferred, but heterologous cells are encompassed within the scope of the invention.

The interrelationship of dosages for animals of various sizes and species and humans based on mg/m.sup.2 of surface area is described by Freireich, E. J., et al. Cancer Chemother., Rep. 50 (4):219–244 (1966). Adjustments in the dosage regimen may be made to optimize the tumor cell growth inhibiting and killing response, e.g., doses may be divided and administered on a daily basis or the dose reduced proportionally depending upon the situation (e.g., several divided dose may be administered daily or proportionally reduced depending on the specific therapeutic situation).

It would be clear that the dose of the molecules of the invention required to achieve cures may be further reduced with schedule optimization.

Use of PEG-promoter to Direct High Expression of a Heterlogous Gene in Cancer Cells One embodiment of the invention provides for methods for expressing a gene of interest which gene is not endogenously expressed in cancer cells which comprises a) constructing a nucleic acid which comprises the PEG-3 promoter operatively linked to the gene-of-interest; b) introducing this nucleic acid into a cancer cell which cell expresses PEG-3, thereby causing the PEG-3 promoter to direct expression of the gene-of-interest in the cancer cell. In one embodiment, the gene-of-interest encodes a protein which is cytotoxic to the cancer cell, causes apoptosis of the cancer cell, slows the growth of the cancer cell, or causes the cancer cell to stop dividing. The gene-of-interest can be any gene whose expression would cause a desired biochemical or physiological effect in the cancer cell, such as the decrease of growth or the decrease or inhibition of cancer phenotype progression.

One advantage of using the nucleic acid construct described above in such a method to treat cancer in a subject, is that the nucleic acid can be administered to both cancerous and normal cells. However, since the PEG-3 promoter is only active in cancerous cells, there will be no expression of the gene-of-interest in normal cells, while there will be high expression of the gene-of-interest in the cancerous cells. This nucleic acid construct thus allows one to target specifically expression of a gene-of-interest to specifically cancerous cells.

Liposomes could be used as a delivery agent to introduce the nucleic acid construct to the cells of the subject to be treated. Of course, there are many ways to deliver such a nucleic acid construct which would be known to one of skill in the art (e.g. microinjection; topical application; use of a chemical vehicle; direct injection into the tumor; etc.).

Expression of the PEG-3 Gene Correlates Directly with the Progression Phenotype in Viral and Oncogene Transformed Rodent Cells. A critical component of cancer development is progression, a process by which a tumor cell develops either qualitatively new properties or displays an increase in the expression of traits that enhance the aggressiveness of a tumor (1–4). Insight into this process offers the potential of providing important new targets for intervening in the neoplastic process (1–4). In the Ad5 transformed RE cell culture model system, enhanced anchorage-independent growth and in vivo tumorigenic aggressiveness, i.e., markers of the progression phenotype, are stable traits that can be induced spontaneously or by gene transfer (oncogenes and growth factor-related genes) (Table 1).

Table 1. Expression of PEG-3 in Ad5-transformed RE cells directly correlates with expression of the progression phenotype

| Cell Type[a] | Agar Cloning Efficiency (%)[b] | Tumorigenicity in Nude Mice[c] | Progression Phenotyped[d] |
|---|---|---|---|
| RE | <0.001 | 0/10 | Prog− |
| CREF | <0.001 | 0/18 | Prog− |
| E11 | 2.9 ± 0.3 | 8/8 (36) | Prog− |
| E11-NMT | 34.3 ± 4.1 | 6/6 (20) | Prog+ |
| CREF X E11-NMT F1 | 2.0 ± 0.3 | 0/6 | Prog− |
| CREF X E11-NMT F2 | 1.5 ± 0.1 | 0/6 | Prog− |
| CREF X E11-NMT R1 | 72.5 ± 9.4 | 3/3 (17) | Prog+ |
| CREF X E11-NMT R2 | 57.4 ± 6.9 | 3/3 (17) | Prog+ |
| E11 X E11-NMT IIId | 5.6 ± 0.7 | 3/3 (56) | Prog− |
| E11 X E11-NMT IIIdTD | 41.0 ± 4.9 | 3/3 (19) | Prog+ |
| E11 X E11-NMT A6 | 0.3 ± 0.0 | 3/3 (44) | Prog− |
| E11 X E11-NMT A6TD | 29.3 ± 3.5 | N.T. | Prog+ |
| E11 X E11-NMT 3b | 1.5 ± 0.2 | 3/3 (31) | Prog− |
| E11 X E11-NMT IIA | 29.5 ± 2.8 | 3/3 (23) | Prog+ |
| E11-NMT AZA C1 | 2.8 ± 0.5 | N.T. | Prog− |
| E11-NMT AZA B1 | 1.6 ± 0.3 | 3/3 (41) | Prog− |
| E11-NMT AZA C2 | 2.0 ± 0.1 | 3/3 (50) | Prog− |
| E11-ras R12 | 36.8 ± 4.6 | 3/3 (18) | Prog+ |
| E11-HPV E6/E7 | 31.7 ± 3.1 | 3/3 (22) | Prog+ |

[a]Cell line descriptions can be found in Materials and Methods.
[b]Anchorage-independent growth was determined by seeding variable numbers of cells in 0.4% agar on a 0.8% agar base layer. Results are the average number of colonies from 4 replicate plates ± S.D.
[c]Tumorigenicity was determined by injecting nude mice with $2 \times 10^6$ or $1 \times 10^7$ (RE, CREF and CREF X E11-NMT hybrids). Results are the number of animals with tumors per number of animals injected and the number in parentheses indicate average latency time in days, i.e., first appearance of a palpable tumor. N.T. = not tested.
[d]Prog− = progression phenotype is not expressed; Prog+ = progression phenotype is expressed.

Upon treatment of progressed cells with AZA, the progression phenotype can be stably reversed (1,10). A reversion of progression also occurs following somatic cell hybridization of progressed cells with unprogressed Ad5-transformed cells or with normal CREF cells. A further selection of these unprogressed Ad5-transformed cells by injection into nude mice results in acquisition of the progressed phenotype following tumor formation and establishment in cell culture. These studies document that progression in this model system is a reversible process that can be stably produced by appropriate cellular manipulation. In this context, the Ad5-transformed RE model represents an important experimental tool for identifying genes that are associated with and that mediate cancer progression.

To directly isolate genes elevated during progression we employed an efficient subtraction hybridization approach previously used to clone the p21 gene (melanoma differentiation associated gene-6; mda-6) (23,25) and a novel cancer growth suppressing gene mda-7 (26,29). For this approach, cDNA libraries from a progressed mutant Ad5 (H5ts125)-transformed RE clone, E11-NMT (10), and its parental unprogressed cells, E11 (10,31), were directionally cloned into the λ Uni-ZAP phage vector and subtraction hybridization was performed between double-stranded tester (E11-NMT) and single-stranded driver DNA (E11) by mass excision of the libraries (23). With this strategy in combination with the RACE procedure and DNA ligation techniques a full-length PEG-3 cDNA displaying elevated expression in E11-NMT versus E11 cells was cloned. Northern blotting analysis indicates that PEG-3 expression is ≧10-fold higher in all progressed Ad5-transformed RE cells, including E11-NMT, specific E11-NMT × CREF somatic cell hybrid clones, R1 and R2, expressing an aggressive transformed phenotype and specific E11× E11-NMT somatic cell hybrid clones, such as IIa that display the progression phenotype (FIG. 1 and Table 1). PEG-3 mRNA levels also increase following induction of progression by stable expression of the Ha-ras and HPV-18 E6/E7 oncogenes in E11 cells (FIG. 1). A further correlation between expression of PEG-3 and the progression phenotype is provided by E11× E11-NMT clones, such as IIId and A6, that initially display a suppression of the progression phenotype and low PEG-3 expression, but regain the progression phenotype and PEG-3 expression following tumor formation in nude mice, i.e., IIIdTD and A6TD (Table 1 and FIG. 1). In contrast, unprogressed Ad5-transformed cells, including E11, E11-NMT × CREF clones F1 and F2, E11× E11-NMT clones IIId, AG and 3b and AZA-treated E11-NMT clones B1, C1 and C2, have low levels of PEG-3 RNA. These results provide evidence for a direct relationship between the progression phenotype and PEG-3 expression in this Ad5-transformed RE cell culture system. They also demonstrate that the final cellular phenotype, i.e., enhanced anchorage-independence and aggressive tumorigenic properties, is a more important determinant of PEG-3 expression than is the agent (oncogene) or circumstance (selection for tumor formation in nude mice) inducing progression.

Figure 2:
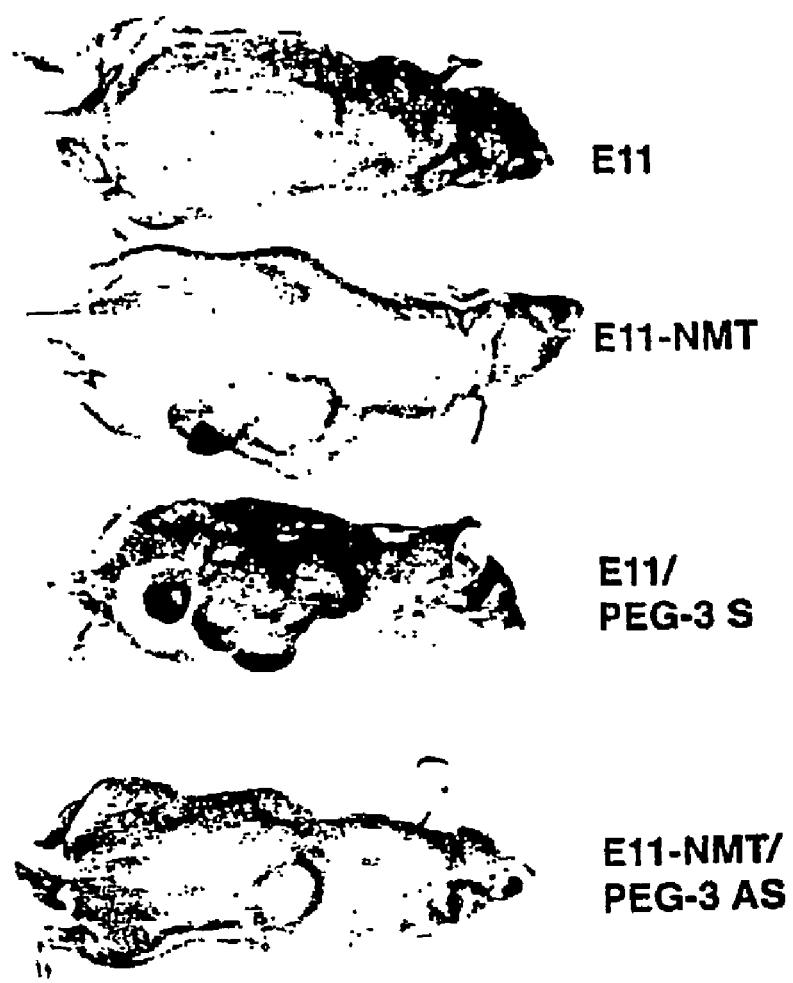
Figure 3A:
Figure 3A:
Figure 3A:
Figure 3A:
Figure 3B:
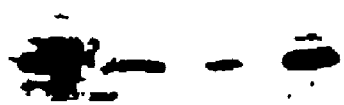

A second rodent model used to study the process of cancer progression employs CREF clones modified by transfection to express dominant acting oncogenes (such as Ha-ras, v-src, HPV-18 and the mutant adenovirus H5 hr1) and tumor suppressor genes (such as Krev-1, RB and wild-type p53) (19–22 and unpublished data). In this model system, Ha-ras-transformed CREF cells are morphologically transformed, anchorage-independent and induce both tumors and lung metastases in syngeneic rats and athymic nude mice (19–22). The Krev-1 (Ha-ras) suppressor gene reverses the in vitro and in vivo properties in Ha-ras transformed cells (21). Although suppression is stable in vitro, Ha-ras/Krev-1 CREF cells induce both tumors and metastases after extended times in nude mice (21). Expression of PEG-3 is not apparent in CREF cells, whereas tumorigenic CREF cells transformed by v-src, HPV-18, H5 hr1 and Ha-ras contain high levels of PEG-3 RNA (FIG. 2). Suppression of Ha-ras induced transformation by Krev-1 inhibits PEG-3 expression. However, when Ha-ras/Krev-1 cells escape tumor suppression and form tumors and metastases in nude mice, PEG-3 expression reappears, with higher expression in metastatic-derived than tumor-derived clones (FIG. 2). These findings provide further documentation of a direct relationship between induction of a progressed and oncogenic phenotype in rodent cells and PEG-3 expression. As indicated above, it is the phenotype rather than the inducing agent that appears to be the primary determinant of PEG-3 expression in rodent cells.

The PEG-3 Gene Displays Sequence Homology with the Hamster gadd34 and Mouse MyD116 Genes and is Inducible by DNA Damage.

Figure 4A:
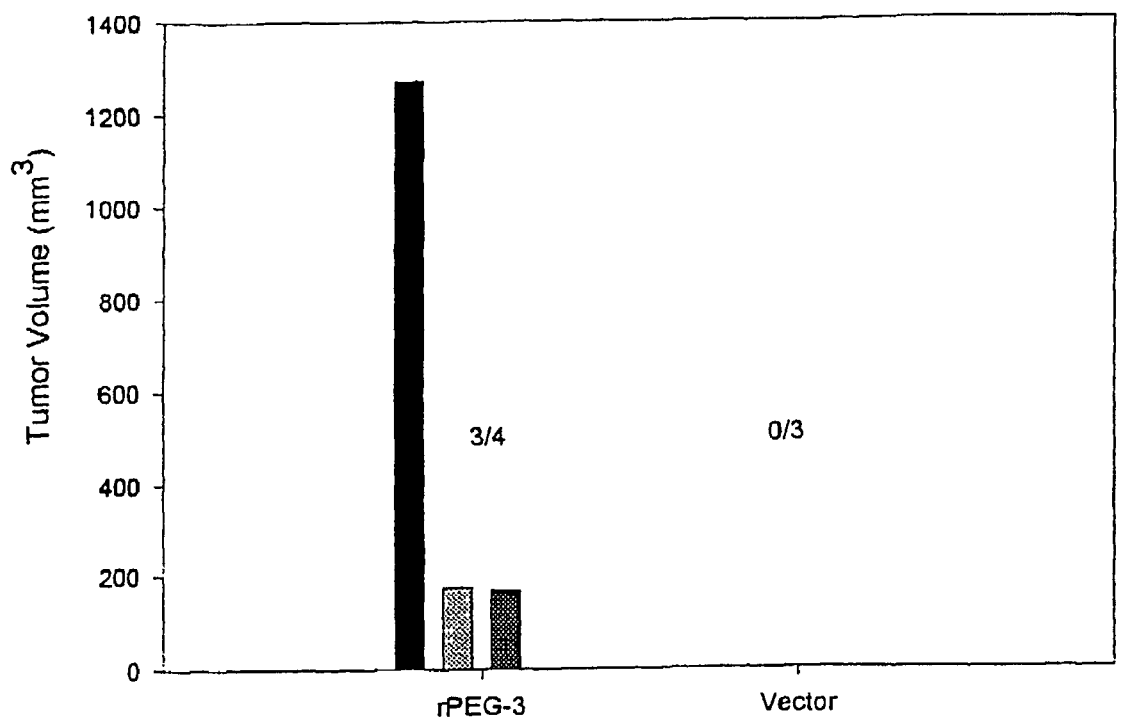
Figure 4B:
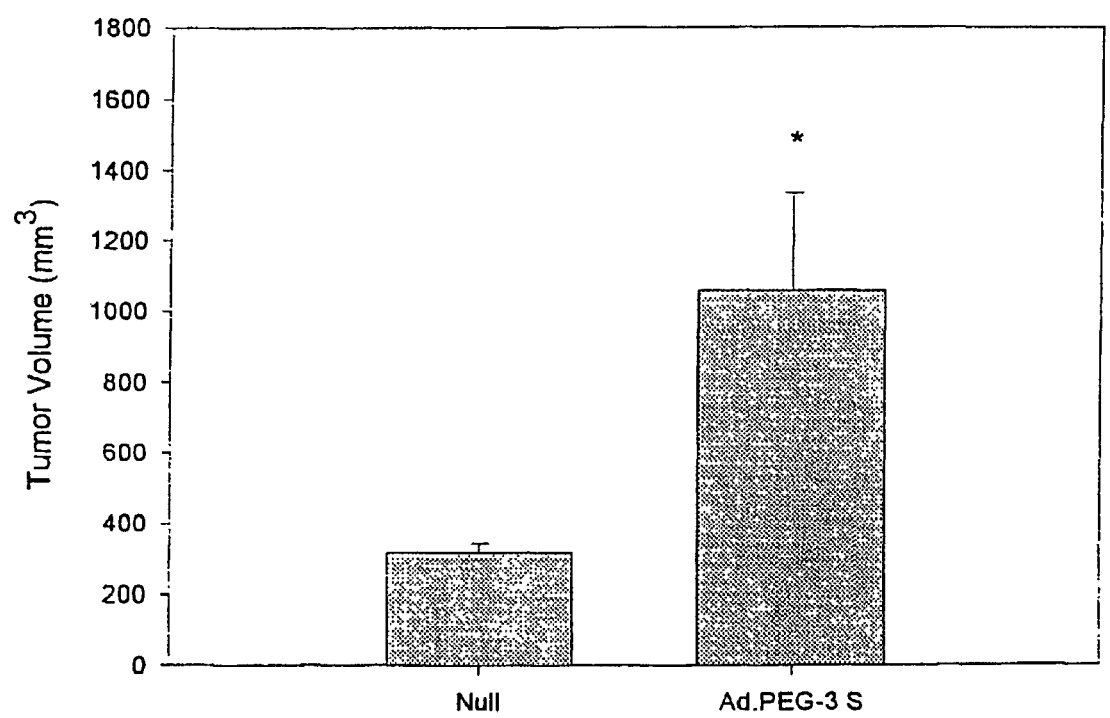

The cDNA sizes of PEG-3, gadd34 and MyD116 are 2210, 2088 and 2275 nt, respectively. The nt sequence of PEG-3 is ~73% and the aa sequence is ~59% homologous to the gadd34 (32) gene (FIG. 3 and data not shown). PEG-3 also shares significant sequence homology, ~68% nt and ~72% aa, with the murine homologue of gadd34, MyD116 (33,34) (FIG. 3 and data not shown). Differences are apparent in the structure of the 3' untranslated regions of PEG-3 versus gadd34/MyD116. ATTT motifs have been associated with mRNA destabilization. In this context, the presence of 3 ATTT sequences in Gadd34 and 6 tandem ATTT motifs in MyD116 would predict short half-lives for these messages. In contrast, PEG-3 contains only 1 ATTT motif suggesting that this mRNA may be more stable. The sequence homologies between PEG-3 and gadd34/MyD116 are highest in the amino terminal region of their encoded proteins, i.e., ~69 and ~76% homology with gadd34 and Myd116, respectively, in the first 279 aa. In contrast, the sequence of the carboxyl terminus of PEG-3 significantly diverges from gadd34/Myd116, i.e., only ~28 and ~40% homology in the carboxyl terminal 88 aa. In gadd34 and MyD116 a series of similar 39 aa are repeated in the protein, including 3.5 repeats in gadd34 and 4.5 repeats in MyD116. In contrast, PEG-3 contains only 1 of these 39 aa regions, with ~64% and ~85% homology to gadd34 and MyD116, respectively. On the basis of sequence analysis, the PEG-3 gene should encode a protein of 457 aa with a predicted MW of ~50 kDa. To confirm this prediction, in vitro translation analyses of proteins encoded by the PEG-3 cDNA were determined (FIG. 4). A predominant protein after in vitro translation of PEG-3 has a molecular mass of ~50 kDa (FIG. 4). In contrast, gadd34 encodes a predicted protein of 589 aa with an $M_w$ of ~65 kDa and MyD116 encodes a predicted protein of 657 aa with an $M_W$ of ~72 kDa.

The profound similarity in the structure of PEG-3 versus gadd34/MyD116 cDNA and their encoded proteins suggest that PEG-3 is a new member of this gene family. Moreover, the alterations in the carboxyl terminus of PEG-3 may provide a functional basis for the different properties of this gene versus gadd34/MyD116.

The specific role of the gadd34/MyD116 gene in cellular physiology is not known. Like hamster gadd34 and its murine homologue MyD116, PEG-3 steady-state mRNA and RNA transcriptional levels are increased following DNA damage by methyl methanesulfonate (MMS) and gamma irradiation (γIR) (FIGS. 2 and 5 and data not shown). In contrast, nuclear run-on assays indicate that only the PEG-3 gene is transcriptionally active (transcribed) as a function of transformation progression (FIG. 5). This is apparent in CREF cells transformed by Ha-ras and in E11-NMT and various E11-NMT subclones either expressing or not expressing the progression phenotype (FIG. 5). The gadd34/MyD116 gene, as well as the gadd45, MyD118 and gadd153 genes, encode acidic proteins with very similar and unusual charge characteristics (24). PEG-3 also encodes a putative protein with acidic properties similar to the gadd and MyD genes (FIG. 3). The carboxyl-terminal domain of the murine MyD116 protein is homologous to the corresponding domain of the herpes simplex virus 1 $\gamma_1 34.5$ protein, that prevents the premature shutoff of total protein synthesis in infected human cells (35,36). Replacement of the carboxyl-terminal domain of $\gamma_1 34.5$ with the homologous region from MyD116 results in a restoration of function to the herpes viral genome, i.e., prevention of early host shutoff of protein synthesis (36). Although further studies are required, preliminary results indicate that expression of a carboxyl terminus region of MyD116 results in nuclear localization (36). Similarly, gadd45, gadd153 and MyD118 gene products are nuclear proteins (24,37). Moreover, both gadd45 and MyD118 interact with the DNA replication and repair protein proliferating cell nuclear antigen (PCNA) and the cyclin-dependent kinase inhibitor p21 (37). MyD118 and gadd45 also modestly stimulate DNA repair in vitro (37). The carboxyl terminus of PEG-3 is significantly different than that of MyD116 (FIG. 3). Moreover, the carboxyl-terminal domain region of homology between MyD116 and the $\gamma_1 34.5$ protein is not present in PEG-3. In this context, the localization, protein interactions and properties of PEG-3 may be distinct from gadd and MyD genes. Once antibodies with the appropriate specificity are produced it will be possible to define PEG-3 location within cells and identify potentially important protein interactions mediating biological activity. This information will prove useful in elucidating the function of the PEG-3 gene in DNA damage response and cancer progression.

PEG-3 Lacks Potent Growth Suppressing Properties Characteristic of the gadd and MyD Genes. An attribute shared by the gadd and MyD genes is their ability to markedly suppress growth when expressed in human and murine cells (24,37). When transiently expressed in various human tumor cell lines, gadd34/MyD116 is growth inhibitory and this gene can synergize with gadd45 or gadd153 in suppressing cell growth (24). These results and those discussed above suggest that gadd34/MyD116, gadd45, gadd153 and MyD118, represent a novel class of mammalian genes encoding acidic proteins that are regulated during DNA damage and stress and involved in controlling cell growth (24,37). In this context, PEG-3 would appear to represent a paradox, since its expression is elevated in cells displaying an in vivo proliferative advantage and a progressed transformed and tumorigenic phenotype.

Figure 6:
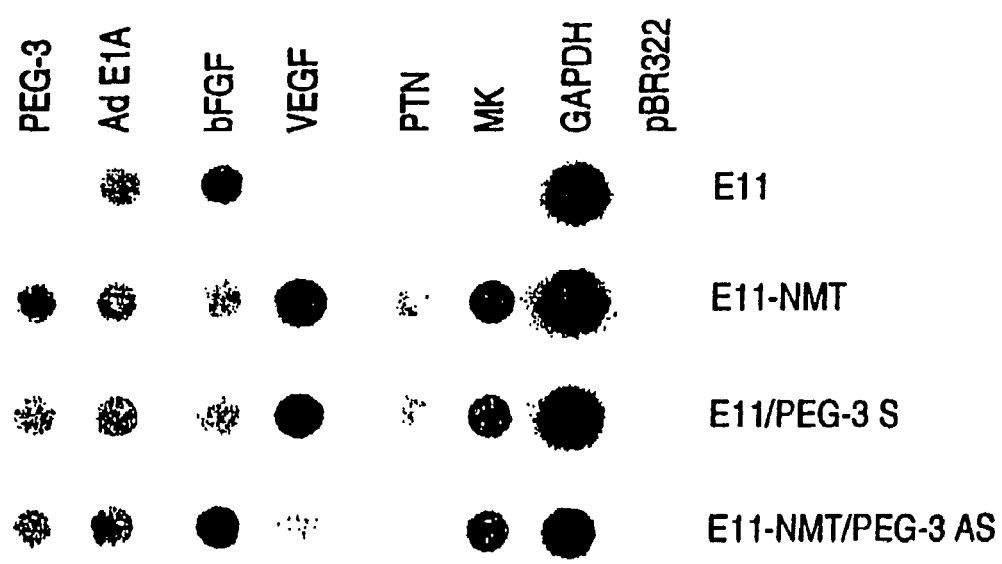

To determine the effect of PEG-3 on growth, E11 and E11-NMT cells were transfected with the protein coding region of the PEG-3 gene cloned into a Zeocin expression vector, pZeosV (FIG. 6). This construct permits an evaluation of growth in Zeocin in the presence and absence of PEG-3 expression. E11 and E11-NMT cells were also transfected with the p21 (mda-6) and mda-7 genes, previously shown to display growth inhibitory properties (25,26,29). Colony formation in both E11 and E11-NMT cells is suppressed 10 to 20%, whereas the relative colony formation following p21 (mda-6) and mda-7 transfection is decreased by 40 to 58% (FIG. 6 and data not shown). Colony formation is also reduced by 10 to 20% when PEG-3 is transfected into CREF, normal human breast (HBL-100) and human breast carcinoma (MCF-7 and T47D) cell lines (data not shown). Although the gadd and MyD genes were not tested for growth inhibition in E11 or E11-NMT cells, previous studies indicate colony formation reductions of >50 to 75% in several cell types transfected with gadd34, gadd45, gadd153, MyD116 or MyD118 (24,37). The lack of dramatic growth suppressing effects of PEG-3 and its direct association with the progression state suggest that this gene may represent a unique member of this acidic protein gene family that directly functions in regulating progression. This may occur by constitutively inducing signals that would normally only be generated during genomic stress. In this context, PEG-3 might function to alter genomic stability and facilitate tumor progression. This hypothesis is amenable to experimental confirmation.

Figure 7:
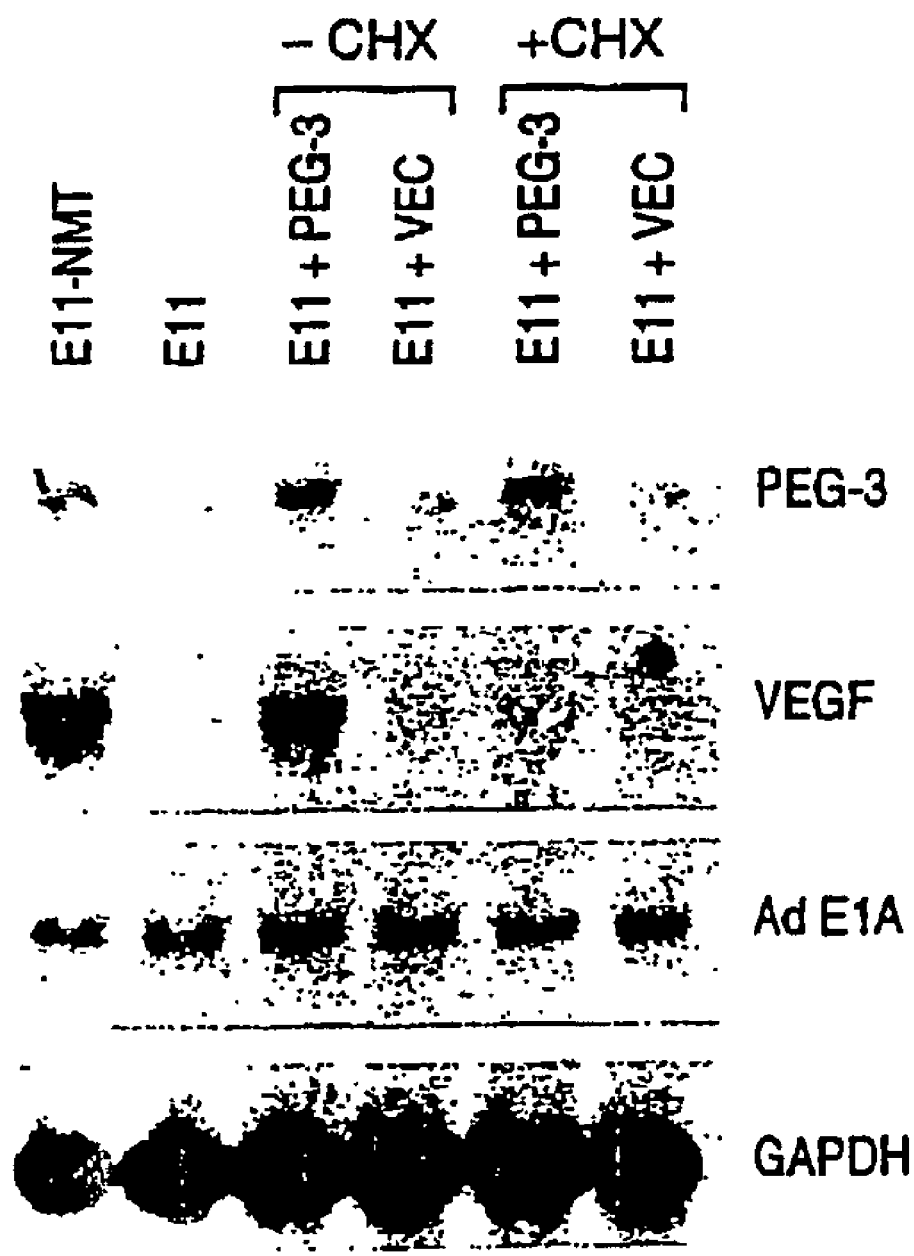
Figure 8:
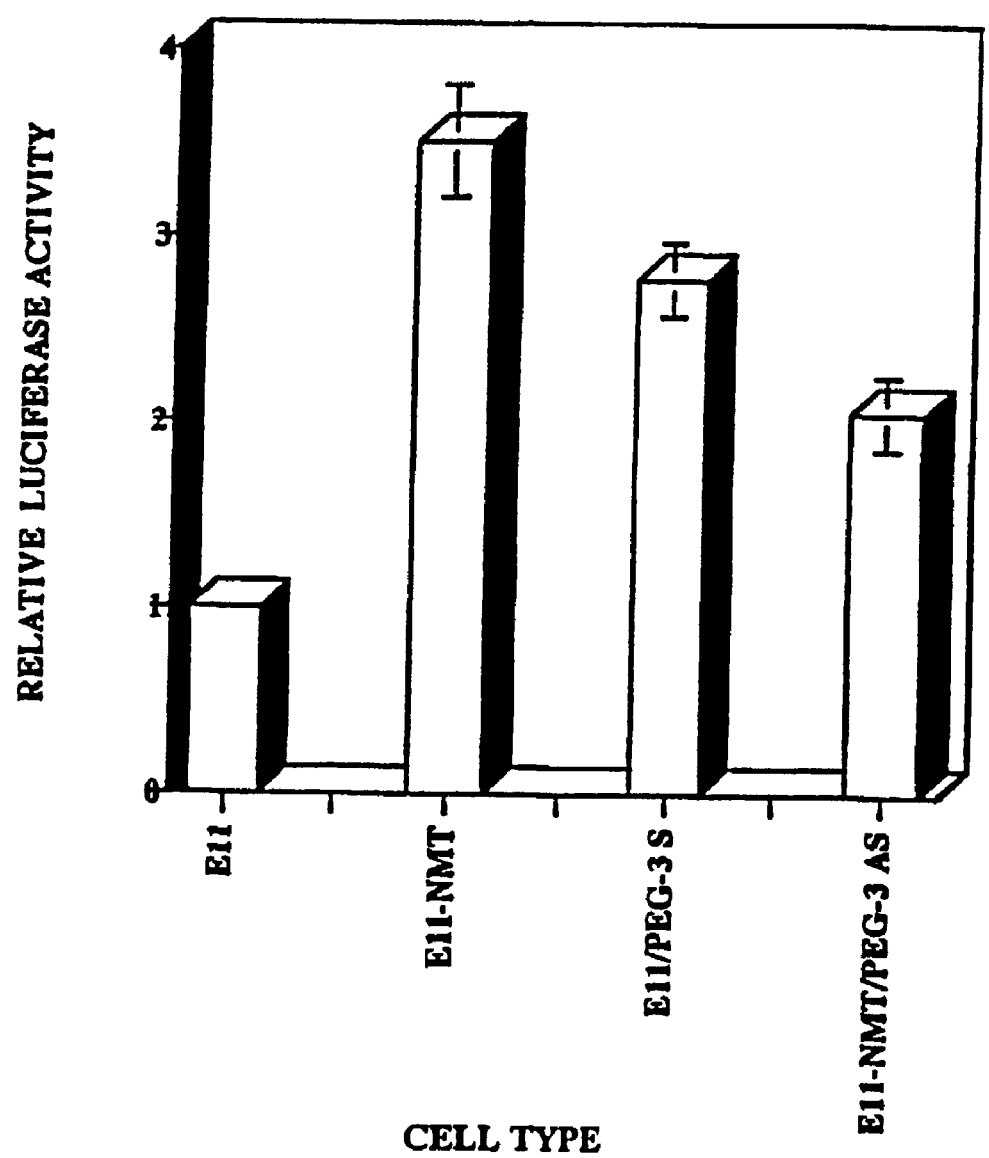

PEG-3 Induces a Progression Phenotype in Ad5-Transformed RE Cells. An important question is whether PEG-3 expression simply correlates with transformation progression or whether it can directly contribute to this process. To distinguish between these two possibilities we have determined the effect of stable elevated expression of PEG-3 on expression of the progression phenotype in E11 cells. E11 cells were transfected with a Zeocin expression vector either containing or lacking the PEG-3 gene and random colonies were isolated and evaluated for anchorage independent growth (FIG. 7). A number of clones were identified that display a 5- to 9-fold increase in agar cloning efficiency in comparison with E11 and E11-Zeocin vector transformed clones. To confirm that this effect was indeed the result of elevated PEG-3 expression, independent Zeocin resistant E11 clones either expressing or not expressing the progression phenotype were analyzed for PEG-3 mRNA expression (FIG. 8). This analysis indicates that elevated anchorage-independence in the E11 clones correlates directly with increased PEG-3 expression. In contrast, no change in Ad5 E1A or GAPDH mRNA expression is detected in the different clones. These findings demonstrate that PEG-3 can directly induce a progression phenotype without altering expression of the Ad5 E1A transforming gene. Further studies are required to define the precise mechanism by which PEG-3 elicits this effect.

Cancer is a progressive disease characterized by the accumulation of genetic alterations in an evolving tumor (1–6). Recent studies provide compelling evidence that mutations in genes involved in maintaining genomic stability, including DNA repair, mismatch repair, DNA replication, microsattelite stability and chromosomal segregation, may mediate the development of a mutator phenotype by cancer cells, predisposing them to further mutations resulting in tumor progression (38). Identification and characterization of genes that can directly modify genomic stability and induce tumor progression will provide significant insights into cancer development and evolution. This information would be of particular benefit in defining potentially novel targets for intervening in the cancer process. Although the role of PEG-3 in promoting the cancer phenotype remains to be defined, the current studies suggest a potential causal link between constitutive induction of DNA damage response pathways, that may facilitate genomic instability, and cancer progression. In this context, constitutive expression of PEG-3 in progressing tumors may directly induce genomic instability or it may induce or amplify the expression of down-stream genes involved in this process. Further studies are clearly warranted and will help delineate the role of an important gene, PEG-3, in cancer.

Subtraction hybridization results in the identification and cloning of a gene PEG-3 with sequence homology and DNA damage inducible properties similar to gadd34 and MyD116. However, PEG-3 expression is uniquely elevated in all cases of rodent progression analyzed to date, including spontaneous and oncogene-mediated, and overexpression of PEG-3 can induce a progression phenotype in Ad5-transformed cells. Our studies suggest that PEG-3 may represent an important gene that is both associated with (diagnostic) and causally related to cancer progression. They also provide a potential link between constitutive expression of a DNA damage response pathway and progression of the transformed phenotype.

This invention is illustrated in the Experimental Details section which follows. These sections are set forth to aid in an understanding of the invention but are not intended to, and should not be construed to, limit in any way the invention as set forth in the claims which follow thereafter.

Experimental Details

Materials and Methods

Cells Lines and Culture Conditions. CREF is a specific clone of Fischer F408 rat embryo fibroblast cells (16). E11 is a single cell clone of H5ts125-transformed Sprague-Dawley secondary rat embryo cells (17). E11-NMT is a subclone of E11 cells derived from a nude mouse tumor (14). E11/PEG-3Scl13 and E11-NMT/PEG-3AScl3 are two Zeocin-resistant clones obtained following transfection with pZeoSV/PEG-3S or pZeoSV/PEG-3AS, respectively, and selected for growth in 500 µg/ml of Zeocin. (Invitrogen, CA). The pZeoSV/PEG-3S and pZeoSV/PEG-3AS expression constructs were generated by subcloning a full-length PEG-3 cDNA into the pZeoSV mammalian expression vector (Invitrogen, CA) in either the sense of antisense orientation. All cultures were maintained in the logarithmic phase of growth in the logarithmic phase of growth in Dulbecco's modified Eagle's medium supplemented with 5% FBS (DMEM-5) at 37° C. in a humidified 5% $CO_2$/95% air incubator. Cells resistant to Zeocin were maintained in medium containing 200 µg/ml of Zeocin.

Construction and Assaying of PEG-3 Adenovirus (Ad) Vector. The recombinant replication-defective Ad.PEG-3S was created in two steps and assayed as described previously for producing and assaying Ad.mda-7 antisense and sense (18,19).

Tumorigenesis Assays. 1. Growth of E11 and Variants in Nude Mice. One million of the following lines were injected subcutaneously into athymic nude mice (NIH Swiss, nu/nu males; Taconic Labs, Germantown, N.Y.; 4 animals/group): E11, E11-NMT, E11/PEG-3Scl13 (E11 stably transfected with the rat PEG-3 cDNA) and E11-NM/PEG-3AScl3 (E11 NMT stably transfected with antisense to rat PEG-3). Animals were followed and tumors measured twice weekly with a caliper and tumor volumes were determined using the formula $\pi/6 \times$larger diameter$\times$[smaller diameter]$^2$. Mice were sacrificed when the average tumor volume within a group was >2000 mm$^3$. Statistical significance between the groups was determined by ANOVA using computer program SigmaStat™. A p value of <0.05 was considered significant. Data is presented as tumor volume +/− the standard deviation over time. Additionally, one set of 2 animals/group were sacrificed when the E11/PEG-3 S tumors reached an average tumor volume of 2000 mm$^3$. These tumors were rapidly excised and fixed in 10% neutral buffered formalin, for use in the immunohistochemical studies.

Effects of Rat PEG-3 on the Growth of T98G Xenografts. The human glioblastoma multiform cell line T98g was stably transfected with rat PEG-3 cDNA or vector using the lipofectamine protocol (18). After drug selection, one million pooled cells from each transfected (PEG-3 or vector) were injected subcutaneously into nude mice (4-animals/group). Animals were followed for 4 months and sacrificed. Tumor volumes were determined s describes above.

Effect of Ad.PEG-3 S Infection on the Growth of DU-145 Xenografts. The human prostate carcinoma cell line DU-145 was infected with the control adenovirus (Ad.Vec) or an adenovirus expressing the rat PEG-3 cDNA (Ad.PEG-3 S). Forty-eight hours after infection, cells were removed with trypsin-EDTA, mixed with Matrigel (1:1 Collaborative Research, Bedford, Mass.) and injected subcutaneously into nude mice. Animals were followed for one month and sacrificed. Tumor volumes were determined as described above.

Immunohistochemistry. Formalin-fixed tumors were embedded in paraffin, sectioned, and mounted on glass slides (20). Sections were deparaffinized through graded xylene and alcohol washes and endogenous peroxidase activity quenched using methanol-hydrogen peroxide. Sections were blocked with 5% goat serum in PBS and a monoclonal antibody to mouse CD31 (PharminGen, CA) added for 1 hour at room temperature. The sections were washed in PBS and antibody binding was determined using a Vector ABC kit (Vector Labs, CA). Following extensive washing, sections were stained with DAB and visualized under the light microscope. In addition to immunostaining, sections were also stained with hematoxylin-eosin to determine tumor morphology and confirm microvessel density.

Nucleic Acid Analyses. Steady-state levels of PEG-3, VEGF, ElA, and GAPHD mRNA were determined by Northern analysis of total cytoplasmic RNA using appropriate multiprimed $^{32}$P-labeled cloned cDNA probes as described previously (18,19). Briefly, 10 µg of total RNA from the different cell types were electrophoresed in a 1% agarose gel, transferred to a nylon membrane and hybridized with the different $^{32}$p-labeled CDNA fragments. The membrane was stripped and hybridized with indicated probes sequentially. Northern blots were washed in a 0.1% SDS, 1×SSC buffer at RT for 30 min followed by washing at 42° C. for an additional 30 min in the same buffer. Nuclear run-on (In Vitro transcription) assays within isolated nuclei were performed as previously described (21, 22). Briefly, nuclei from 10$^7$ cells were isolated and RNA transcripts previously initiated by RNA polymerase II were allowed to elongate in the presence of $^{32}$P-UTP (100 µci, 3000 Ci/mmol.) The $^{32}$P-labeled RNA was extracted with phenol/chloroform and unincorporated nucleotides were removed by passing the probe through a G-50 sephadex column. Nylon membranes containing 10 µg of the appropriate denatured plasmid DNA gene insert were hybridized with the $^{32}$P-labeled RNA. Nylon membranes contained PEG-3, AdE1A, bFGF, VEGF, PTN, MK, GAPDH and pBR322 DNA probes. Following hybridization, the Nylon membranes were washed and exposed for autoradiography.

Western Blotting Analyses. Secreted VEGF protein was monitored by Western blot analysis as previously described (23). Five million cells were seeded into a 100-mm/tissue culture plate and incubated for 24 hr at 37° C. The medium (DMEM-5) was removed and the cells were washed 5× with DMEM without FBS (DMEM-O). Five ml of DMEM-O were added to each plate and the cells were incubated for 36 hr at 37° C. The media from the different cell types were harvested and concentrated to 100 µl using a Centricon filter (Amicon Cat No: 4211, Beverly, Mass.). The levels of secreted VEGF protein were determined by western blotting by ECL (Amersham, Ill. Cat No: RPN 2108) and anti-VEGF antibody® & D, WI).

VEGF-Promoter Luciferase Assay. A mouse VEGF promoter (24) (provided by Dr. A. P. Adamis, Boston, Mass.) was subcloned from pGL2BV1.6 vector into the pGL3-basic Luciferase reporter vector (Promega E1751). The different cell types were seeded at 5×10$^5$ cells/35 mm plate 24 hr prior to transfection. Cells were cotransfected with 5 µg of the pGL3/VEGF vector and 1 µg of the pSV-Beta-galactosidase vector (Promega E1081) with 10 µl of Lipofectamin (Gibco, N.Y.). After 48 hr incubation at 37° C., cell lysates were prepared and the luciferase activity was determined using a Luciferase Reporter Gene Assay kit (Boehringer-Mannheim, Ind.). The beta-gal activity was determined using the Galacto-Light Plus kit (Tropix, Mass.). The luciferase data were standardized relative to beta-gal activity. To determine the effect of ectopic expression of PEG-3 on VEGF promoter activity in human tumor cells, cultures were infected with 100 pfu/cell of Ad.PEG-3 or Ad. Vec (Ad lacking the PEG-3 gene insert), 24 hr later cells were transfected with pGL3/VEGF and pSV-Beta galactosidase vectors and 48 hr later luciferase and beta-galactosidase activity was determined as described above.

Results

PEG-3 lacks transforming or tumor inducing potential when expressed in normal cloned rat embryo fibroblast cells. Experiments were conducted to determine if PEG-3 is transforming or oncogenic when expressed in normal rat embryo fibroblast cells. CREF cells were transfected with PEG-3 cloned in an expression plasmid containing a Zeocin resistance gene (3). Transfected cells were selected for Zeocin resistance and evaluated for transformed focus formation in cell culture. Additionally, transfected and antibiotic resistant selected cultures were pooled and injected into nude mice to identify clones with tumorigenic potential. Under these experimental conditions, PEG-3 failed to induce a transformed or oncogenic phenotype (data not shown). In contrast, high-molecular weight DNA from various human tumor cell lines (including human prostate carcinoma, breast carcinoma and glioblastoma multiforme), a primary tumor from a metastasis from a patient with colorectal carcinoma and various cloned oncogenes, including Ha-ras, Ad E1A, v-src, human papilloma virus type 18 and v-raf, induce morphological transformation in culture and/or an oncogenic phenotype in CREF cells (15,25,26). These findings demonstrate that PEG-3 does not function as a classical oncogene, whereas it can modify the phenotype of previously transformed cells (3).

Elevated expression of PEG-3 in transformed rodent and human tumor cells directly correlates with an aggressive tumor phenotype in nude mice. To evaluate the oncogenic potential of cells expressing PEG-3, nude mice were injected subcutaneously with transformed rodent cells endogenously or ectopically expressing PEG-3, E11-NMT and E11/PEG-3 S, respectively, or expressing reduces levels of PEG-3, E11-NMT/PEG-3 AS, respectively (FIG. 1). Inoculation of nude mice with E11-NMT or E11/PEG-3S (three independent clones of E11 cells genetically engineered to express elevated levels of PEG-3) resulted in the formation of aggressive, highly vascularized and rapidly growing tumors (FIGS. 1 and 2). In contrast, injection of nude mice with E11 or E11-NMT/PEG-3 AS (two independent clones of E11-NMT cells stably expressing antisense PEG-3 and displaying diminished PEG-3 expression) formed slow growing, compact and poorly vascularized tumors (FIGS. 1 and 2). FIG. 1 shows representative data for a 20 day study using E11/PEG-3 S cl 13 and E11-NMT/PEG-3 As cl 3; animals were sacrificed at this time because of regulations regarding tumor size. In a separate study, animals injected with E11-NMT/PEG-3 AS cl 3 cells were maintained for 50 days at which time the final tumor size was still smaller than observed after 20 days in animals injected with E11-NMT/PEG-3 S cl 13 (data not shown). Analysis of mRNAs in the different cell strains demonstrated that tumor size and vascularization directly correlate with steady state PEG-3 mRNA levels, which are elevated in the aggressive tumor forming cell lines (FIG. 3 and data not shown).

To determine if PEG-3 could also regulate cancer aggressiveness in human tumor cells, T98G human glioblastoma multiforme cells were genetically modified by DNA transection to express the rat PEG-3 coding region. Parental T98G cells did not express PEG-3 or form tumors (after 10 weeks) in nude mice, whereas 75% of animals injected with PEG-3 transfected T98G cells produced tumors (FIG. 4). Tumors that developed in the nude mice injected with PEG-3 transfected T98G cells expressed rat PEG-3 (data not shown). Likewise, infection of DU-145 human prostate carcinoma cells with a replication defective type 5 adenovirus expressing PEG-3, Ad.PEG-3S, 48 hr prior to injection into nude mice resulted in more rapid tumor development and statistically significant increase in tumor volume ($p<0.025$) (FIG. 4). Moreover, induction of elevated rat PEG-3 expression in diverse human tumors by infection with Ad.PEG-3S, including carcinomas of the breast (MCF-7 and T47D), cervix (HeLa) and prostate (DU-145), enhanced anchorage independent growth (data no shown). These results document that the rat PEG-3 gene can induce an aggressive oncogenic phenotype and enhance expression of the transformed state in both rodent and human tumor cells.

Figure 5A:
Figure 5B:
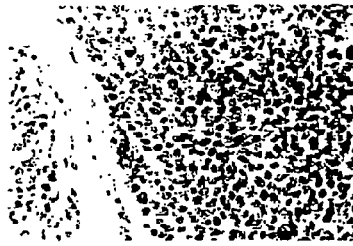
Figure 5C:
Figure 5D:
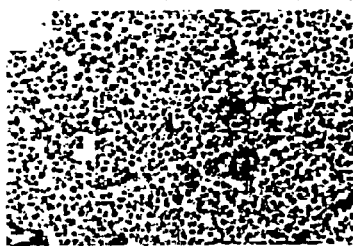
Figure 5E:
Figure 5F:
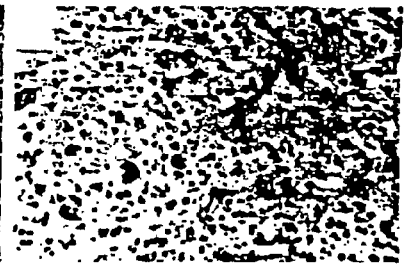
Figure 5G:
Figure 5H:

PEG-3 expression correlates with elevated angiogenesis and increased VEGF expression. On the basis of the morphology of tumors in nude mice induced by PEG-3 expressing rodent tumor cells (highly vascularized and bloody, FIG. 2) we focused on angiogenesis as a possible process underlying the increased in vivo aggressiveness of these tumor cell lines. Analysis of tumors isolated after injection of the different cell strains in nude mice indicated increased formation of blood vessels and elevated CD31 expression, an endothelial cell marker, in PEG-3 expressing transformants (FIG. 5 and data not shown). Similar results were also obtained using monoclonal antibodies to a second endothelial marker, Factor VIII (data not shown). E11-NMT and E11/PEG-3 S cl 13 sections contain multiple microvessels defined by the presence of red blood cells (FIGS. 5C and 5E) and by CD31 staining (FIGS. 5D and 5F). Both E11 and E11-NMT/PEG-3AScl3 contain fewer blood micro vessels. In addition, E11 and E11-NMT/PEG 3AScl three tumors appear "ordered" and show fibrotic regions, which are not seen in the E11-NMT or E11/PEG-3 S sections (FIG. 5).

Analysis of mRNAs isolated from the different cell lines indicated higher VEGF mRNA levels in aggressive PEG-3 expressing tumors cells (FIG. 3). In contrast, the MRNA levels of other recognized modulators of angiogenesis, including basic fibroblast growth factor (bFGF) (2,27), pleiotropic (PTN) (28,29) and midline (MK) (28,29), did not display consistent alterations as a function of PEG-3 expression (data not shown). Analysis of cell supernatants from the different cell types indicated that the level of secreted VEGF protein was increased in E11-NMT and E11/PEG-3S cultures versus E11 and E11-NMT/PEG-3 AS cultures. These results confirm that PEG-3 expression directly correlates with tumor aggressiveness and this process associates with elevated expression of the specific angiogenesis regulator VEGF.

Experiments were performed to define the relationship between PEG-3 and VEGF expression. Nuclear run-on assays documented an association between an elevated rate of PEG-3 transcription and increased VEGF transcription in E11-NMT and E11/PEG-3 S cells (FIG. 6). In contrast, although PEG-3 transcription was elevated in E11-NMT/PEG-3 AS cells, VEGF transcription was only marginally higher than in E11 cells. Since antisense inhibition of gene expression can occur at multiple levels, it is possible that the ability of PEG-3 antisense to decrease steady-state PEG-3 mRNA (FIG. 3) occurs at a post-transcriptional level. Confirmation of elevated transcription of the VEGF gene in PEG-3 expressing rodent tumor cells was also obtained by transient expression studies with a VEGF promoter-luciferase reporter construct (FIG. 7). In these experiments, VEGF promoter activity was highest in E11-NMT/PEG-3 cells with decreased activity in E11-NMT/PEG-3AS cells and the lowest activity in E11 cells. MK transcription was also elevated in E11, E11-NMT and E11-NMT/PEG 3 AS cells, whereas no relationship between PEG-3 and bFGF transcription was apparent and PTN transcription was minimal in all four cell types (FIG. 6). The significance of enhanced MK transcription is unclear since no consistent change in steady-state MK mRNA levels were apparent in the different cell types. These studies document a direct correlation between expression of an aggressive oncogenic phenotype by transformed tumorigenic rodent cells and elevated PEG-3 and VEGF transcription.

To examine further the relationship between PEG-3 and VEGF, experiments were performed to determined if transient ectopic expression of PEG-3 in rodent and human tumor cells could elevate VEGF expression. E11 cells were transfected with a PEG-3 expression construct, nuclei were isolated and evaluated for elevated VEGF transcription and total cytoplasmic RNA was isolated and steady-state VEGF mRNA levels were determined by Northern blotting (FIG. 8 and data not shown). These studies were performed in the presence and absence of cycloheximide to determine if PEG-3 protein was necessary to modify VEGF expression. Elevated VEGF transcription and steady-state RNA levels were apparent in E11 cells 30 hr after transfection with a PEG-3 expression vector, effects that were prevented by cycloheximide (FIG. 8 and data not shown). No changes occurred in the levels of the Ad 5 E1A or GAPDH genes in cycloheximide-treated E11 cells transfected with PEG-3. To determine if elevating rat PEG-3 expression in human cells could also modify VEGF transcription, a series of human carcinoma cells, including breast (T47D), cervix (HeLa) and prostate (DU-145), were infected with 100 pfu/cell of Ad.PEG-3 S and transfected with the VEGF promoter-luciferase reporter construct. Under these experimental conditions the levels of luciferase activity were increased in all of the human carcinoma cell types infected with Ad.PEG-3 S (data not shown). These results suggest that regulation of VEGF expression occurs downstream of PEG-3 expression.

Discussion

PEG-3 represents a unique genetic component of the cancer paradigm. It lacks archetypal oncogenic potential, but can directly facilitate expression of an aggressive cancer phenotype in both rodent and human tumor cells. The present study provides evidence for a relationship between PEG-3 expression and transcriptional activation of the angiogenic regulating molecule VEGF. In this context, PEG-3 may directly contribute to cancer aggressiveness by facilitating blood flow to the tumor resulting in increased growth and access to the circulatory system by potentially metastic tumor cells. Although one level by which PEG-3 regulates VEGF expression involves enhanced transcriptional control, further studies are required to determine if PEG-3 can also affect the processing of VEGF mRNA or RNA or its translation or secretion from tumor cells. In addition, since elevated PEG-3 expression also augments anchorage independent growth in tumor cells, increased cancer aggressiveness may also reflect additional changes in cancer cell physiology resulting in increased tumor growth in vivo. A recently developed gene cloning approach, reciprocal subtraction differential RNA display (RSDD) (4), resulted in the identification of several novel genes displaying either elevated (PEGen) or suppressed (PSGen) expression as a function of transformation progression in the E11 to E11-NMT model. The role of these genes in the progression process and how they interact with PEG-3 in regulating cancer progression are interesting and relevant questions currently under investigation.

The mechanism by which PEG-3 modifies the cancer phenotype remains to be elucidated. PEG-3 is inducible in normal rat embryo cells by DNA damage and expression is elevated as a function of both cancer progression and oncogene-mediated transformation (3). The ability of PEG-3 expression to be induced in CREF cells by DNA damage is shared with two genes with significant homology to PEG-3, a growth arrest and DNA damage inducible hamster gene, gadd34 (30), and its homologous differentiation regulated murine gene, MyD116(31). However, in contrast to these structurally related genes, only PEG-3 expression coincides with the progression phenotype (3). Additional support for a relationship between PEG-3 expression, cancer progression and angiogenes is provided by antisense PEG-3 studies. Expression of PEG-3 antisense in E11-NMT cells suppresses the progression phenotype and reduces VEGF steady state mRNA and secretion. In this context, PEG-3 expression may serve as a sensitive biosensor for identifying therapeutic agents and chemically generated small molecules that can function as novel inhibitors of cancer progression and angiogenesis.

Diverse acting oncogenes, including Ha-ras, v-src, H5 hrl, v-raf and HPV-18, induce a tumorigenic phenotype in CREF cells which correlates with elevated expression of PEG-3. Since the mode of action of these diverse acting oncogenes is different, PEG-3 may represent a common downstream target gene required for the activation of oncogenic potential by cancer cells. Although its role in the multistep carcinogenic process requires further clarification, PEG-3 may function as a "gatekeeper" that regulates the final cascade of gene expression changes required for a cancer cell to progress to a more aggressiveness state (3). Identification of these cancer regulatory molecules should provide insights into the complex controls and processes underlying cancer evolution.

Although the mechanism by which PEG-3 expression positively influences the carcinogenic process remains to be defined, PEG-3 may potentiate this process by eliciting a constitutive DNA damage stress response that facilitates genomic instability and cancer progression, by inducing an aggressive cancer phenotype and angiogenesis. Defining the mode of action of PEG-3 is clearly a worthwhile endeavor and offers promise for identifying relevant target molecules and pathways that may be exploitable for cancer diagnosis and therapy.

References

2. Fisher, P. B. (1984) in *Tumor Promotion and Cocarcinogenesis In Vitro: Mechanisms of Tumor Promotion*, ed. Slaga, T. J. (CRC, Boca Raton, Fla.), pp. 57–123.
3. Fidler, I. J. (1990) *Cancer Res.* 50, 6130–6138.
4. Su, Z.-z., Shi, Y. & Fisher, P. B. (1997) *Proc. Natl. Acad. Sci. USA* 94, 9125–9130
5. Kang, D.-C., LaFrance, R., Su, Z.-z. & Fisher, P. B. (1998) *Proc. Natl. Acad. Sci. USA* 95, 13788–13793
6. Folkman, J. (1990) *J. Natl. Cancer Inst.* 82, 4–6.
7. Folkman, J. (1992) *Semin. Cancer Biol.* 3, 65–71
8. Folkman, J. (1995) *Nature Med.* 1, 27–31
9. Liotta, L. A. & Stetler-Stevenson, W. G. (1991) *Cancer Res.* 51, 5054s–5059s.
10. Kumar, R. & Fidler, I. J. (1998) *In Vivo* 18, 27–34.
11. Weidner, N., Folkman, J., Pozza, F., Bevilacqua, P., Alfred, E. N., Moore, D. H., Meli, S. & Gaspanni, G. (1992) *J. Natl. Cancer Inst.* 84, 1875–1877.
12. Weider, N., Carroll, P. R., Flax, J., Blumenfeld, W. & Folkman, J. (1993) *Am. J. Pathol.* 143, 401–409.
13. Weider, N. & Folkman, J. (1996) in *Important Advances in Oncology*, eds. DeVita, V. T., Hellman, S, & Rosenberg, S. A. (Lippincott-Raven Publishers, Philadelphia, Pa.), pp. 167–190.

14. Fisher, P. B., Bozzone, J. H. & Weinstein, I. B. (1979) *Cell* 18, 695–705.
15. Babiss, L. E., Zimmer, S. G. & Fisher, P. B. (1995) *Science* 228, 1099–1101
16. Fisher, P. B., Babiss, L. E., Weinstein, I. B. & Ginsberg, H. S. (1982) *Proc. Natl. Acad. Sci. USA* 79, 3527–3531.
17. Reddy, P. G., Su. Z.-z & Fisher, P. B. (1993) in Chromosome and Genetic Analysis, Methods in Molecular Genetics, ed. Adolph K. W. (Academic Press, Orlando, Fla.), vol. 1, pp. 68–102.
18. Fisher, P. B., Eisenberg, D., Weinstein, I. B. & Ginsberg H. S. (1978) *Proc. Natl. Acad. Sci. USA* 75, 2311–2314.
19. Jiang, Lin, J. J., Goldstein, N. I., Young, C. S. H. & Fisher, P. B. (1996) *Proc. Natl. Acad. Sci. USA* 93, 9160–9165.
20. Su, Z.-z., Madireddi, M. T., Lin, J. J., Young, C. S. H., Kitada, S., Reed, J. C., Goldstein, N. I. & Fisher, P. B. (1998) *Proc. Natl. Acad. Sci. USA* 95, 14400–14405.
21. Su, Z.-z., Lin, J., Shen, R. Fisher, P. A. Goldstein, N. I. & Fisher, P. B. (1996) *Proc. Natl. Acad. Sci. USA* 93, 7252–7257.
22. Su, Z, Austin & Fisher, P. B. (1993) *Oncogene* 8, 1211–1219.
23. Jiang, et al. (1993) *Mol. Cell. Different.* 1, 197–214.
24. Su., Yemul, S., Estabrook, A., Zimmer, S. G., Friedman, R. M. & Fisher, P. B. (1995) *Intl. J. Oncology* 7, 1279–1284.
25. Shima, D. T., Kuroki, M., Deutsch, U., Ng, Y.-& D'Amore, P. A. (1996) *J. Biol. Chem.* 271, 3877–3833.
26. Su, Z-z., Yemul, S., Estabrook, A., Zimmer, S. G., & Fisher, P. B. (1992) *Anticancer Res.* 12 297–304
27. Lin, J., Su, Z.-z., Grunberger, D., Zimmer, S. G. & Fisher, P. B. (1994) *Intl. J. Onoclogy* 5, 5–15.
28. Folkman, J. & Klagsbrun, M. (1987) *Science* 235, 442–447.
29. Bohlen, P. & Kovesdi, I. (1991) *Prog. Growth Factor Res.* 3, 143–157.
30. Graver, R. I. Radford, D. M., Doris-Kellen, H., Wick, M. R. & Miller, P. G. (1994) *Cancer (Phila.)* 74, 1584–1590.
31. Formace, A. J., Jr., Alamo, I., Jr., & Hollander, M. C. (1988) *Proc. Natl. Acad. Sci. USA* 85, 8800–8804.
32. Lord, K. A., Hoffman-Liebermann, B. & Liebermann, D. A. (1990) *Nucleic Acids Res.* 18, 2823.

What is claimed is:

1. A method for identifying a compound which inhibits angiogenesis in a tumor which comprises:
    a) contacting a cancer cell with a compound to be tested, wherein the cancer cell normally expresses a PEG3 gene;
    b) measuring PEG3 gene expression in the cancer cell;
    c) determining whether PEG3 gene expression has been inhibited, wherein inhibition of PEG3 gene expression indicates the identification of a compound which inhibits angiogenesis.

2. The method of claim 1, wherein the compound is a nucleic acid, a polypeptide or an organic molecule.

* * * * *